United States Patent
Gorin et al.

(10) Patent No.: US 12,269,802 B2
(45) Date of Patent: Apr. 8, 2025

(54) PROCESS FOR PREPARING 2-[[5-(3-CHLOROPHENYL)-3-HYDROXYPYRIDINE-2-CARBONYL] AMINO] ACETIC ACID

(71) Applicant: Akebia Therapeutics, Inc., Cambridge, MA (US)

(72) Inventors: Boris I. Gorin, Oakville (CA); Christopher M. Lanthier, Burlington (CA); Anne Buu Chau Luong, Mississauga (CA); James Densmore Copp, Bargersville, IN (US); Javier Gonzalez, Lafayette, IN (US); Sascha Jautze, Piscataway, NJ (US); Erich Kraus, Essen (DE); Alan O'Connor, Piscataway, NJ (US)

(73) Assignee: Akebia Therapeutics, Inc., Cambridge, MA (US)

( * ) Notice: Subject to any disclaimer, the term of this patent is extended or adjusted under 35 U.S.C. 154(b) by 0 days.

(21) Appl. No.: 18/334,101

(22) Filed: Jun. 13, 2023

(65) Prior Publication Data
US 2024/0158354 A1    May 16, 2024

Related U.S. Application Data

(62) Division of application No. 17/053,614, filed as application No. PCT/US2019/031310 on May 8, 2019, now Pat. No. 11,713,298.

(60) Provisional application No. 62/669,135, filed on May 9, 2018.

(51) Int. Cl.
C07D 213/81    (2006.01)

(52) U.S. Cl.
CPC .................. C07D 213/81 (2013.01)

(58) Field of Classification Search
CPC ..................................... C07D 213/81
USPC ....................................... 546/298
See application file for complete search history.

(56) References Cited

U.S. PATENT DOCUMENTS

| | | |
|---|---|---|
| 3,655,679 A | 4/1972 | Shen et al. |
| 3,703,582 A | 11/1972 | Shen et al. |
| 3,894,920 A | 7/1975 | Kondo et al. |
| 4,016,287 A | 4/1977 | Eberhardt et al. |
| 5,397,799 A | 3/1995 | Kress et al. |
| 5,405,613 A | 4/1995 | Rowland |
| 5,607,954 A | 3/1997 | Weidmann et al. |
| 5,610,172 A | 3/1997 | Weidmann et al. |
| 5,620,995 A | 4/1997 | Weidmann et al. |
| 5,620,996 A | 4/1997 | Weidmann et al. |
| 5,658,933 A | 8/1997 | Weidmann et al. |
| 5,719,164 A | 2/1998 | Weidmann et al. |
| 5,726,305 A | 3/1998 | Weidmann et al. |
| 6,020,350 A | 2/2000 | Weidmann et al. |
| 6,093,730 A | 7/2000 | Weidmann et al. |
| 6,159,379 A | 12/2000 | Means et al. |
| 6,420,427 B1 | 7/2002 | Takahashi et al. |
| 6,566,088 B1 | 5/2003 | Mcknight et al. |
| 6,589,758 B1 | 7/2003 | Zhu |
| 7,183,287 B2 | 2/2007 | Durley |
| 7,323,475 B2 | 1/2008 | Arend et al. |
| 7,588,924 B2 | 9/2009 | Evdokimov et al. |
| 7,811,595 B2 | 10/2010 | Kawamoto et al. |
| 8,050,873 B2 | 11/2011 | Evdokimov et al. |
| 8,124,582 B2 | 2/2012 | Guenzler-Pukall et al. |
| 8,129,376 B2 | 3/2012 | Sundaresan et al. |
| 8,273,773 B2 | 9/2012 | Brameld et al. |
| 8,323,671 B2 | 12/2012 | Wu et al. |
| 8,343,952 B2 | 1/2013 | Wu et al. |
| 8,512,972 B2 | 8/2013 | Evdokimov et al. |
| 8,530,404 B2 | 9/2013 | Seeley et al. |
| 8,598,210 B2 | 12/2013 | Kawamoto et al. |
| 8,722,895 B2 | 5/2014 | Kawamoto et al. |
| 8,865,748 B2 | 10/2014 | Shalwitz et al. |

(Continued)

FOREIGN PATENT DOCUMENTS

| | | |
|---|---|---|
| CA | 2098158 A1 | 12/1993 |
| CA | 2253282 A1 | 11/1997 |

(Continued)

OTHER PUBLICATIONS

American Diabetes Association, "Standards of Medical Care in Diabetes-2006", Diabetes Care, vol. 29, Suppl. 1, Jan. 2006, pp. S4-S42, (39 pages).

(Continued)

*Primary Examiner* — Niloofar Rahmani
(74) *Attorney, Agent, or Firm* — Proskauer Rose LLP

(57) ABSTRACT

Disclosed herein are methods and processes of preparing vadadustat and pharmaceutically acceptable salts thereof, and intermediates of formula (I) and their salts useful for the synthesis of vadadustat.

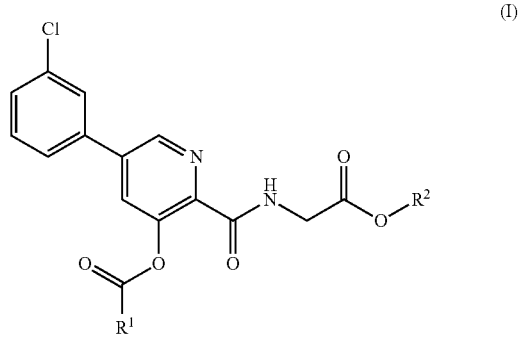

(I)

17 Claims, No Drawings

(56) References Cited

U.S. PATENT DOCUMENTS

| | | | |
|---|---|---|---|
| 8,940,773 | B2 | 1/2015 | Kawamoto et al. |
| 9,145,366 | B2 | 9/2015 | Lanthier et al. |
| 9,598,370 | B2 | 3/2017 | Kawamoto et al. |
| 9,701,636 | B2 | 7/2017 | Copp et al. |
| 9,776,969 | B2 | 10/2017 | Lanthier et al. |
| 9,987,262 | B2 | 6/2018 | Copp et al. |
| 10,149,842 | B2 | 12/2018 | Copp et al. |
| 10,150,734 | B2 * | 12/2018 | Hanselmann .......... A61P 35/00 |
| 10,246,416 | B2 | 4/2019 | Lanthier et al. |
| RE47,437 | E | 6/2019 | Kawamoto et al. |
| 10,596,158 | B2 | 3/2020 | Copp et al. |
| 10,729,681 | B2 | 8/2020 | Kawamoto et al. |
| 10,738,010 | B2 | 8/2020 | Lanthier et al. |
| 11,713,298 | B2 * | 8/2023 | Gorin ................... C07D 213/81 |
| | | | 546/298 |
| 2002/0192737 | A1 | 12/2002 | Kaelin et al. |
| 2003/0153503 | A1 | 8/2003 | Klaus et al. |
| 2003/0176317 | A1 | 9/2003 | Guenzler-Pukall et al. |
| 2004/0235082 | A1 | 11/2004 | Fourney et al. |
| 2004/0254215 | A1 | 12/2004 | Arend et al. |
| 2006/0142389 | A1 | 6/2006 | Aurell et al. |
| 2006/0276477 | A1 | 12/2006 | Klaus et al. |
| 2007/0105899 | A1 | 5/2007 | Suzuki et al. |
| 2007/0154482 | A1 | 7/2007 | Sukhatme et al. |
| 2007/0203174 | A1 | 8/2007 | Klimko et al. |
| 2007/0213335 | A1 | 9/2007 | Fitch et al. |
| 2007/0299086 | A1 | 12/2007 | Kawamoto |
| 2008/0124740 | A1 | 5/2008 | Evdokimov et al. |
| 2008/0213404 | A1 | 9/2008 | Johnson et al. |
| 2009/0023666 | A1 | 1/2009 | Gardiner et al. |
| 2009/0082357 | A1 | 3/2009 | Fitch et al. |
| 2009/0240475 | A1 | 9/2009 | Evdokimov et al. |
| 2010/0021423 | A1 | 1/2010 | Brameld et al. |
| 2010/0331303 | A1 | 12/2010 | Kawamoto et al. |
| 2010/0331374 | A1 | 12/2010 | Wu et al. |
| 2011/0077400 | A1 | 3/2011 | Lobben et al. |
| 2011/0305776 | A1 | 12/2011 | Ho et al. |
| 2012/0282627 | A1 | 11/2012 | Evdokimov et al. |
| 2012/0309977 | A1 | 12/2012 | Lanthier et al. |
| 2012/0316204 | A1 | 12/2012 | Shalwitz et al. |
| 2012/0329836 | A1 | 12/2012 | Marsh et al. |
| 2013/0022974 | A1 | 1/2013 | Chinnaiyan et al. |
| 2013/0203816 | A1 | 8/2013 | Kawamoto et al. |
| 2013/0245076 | A1 | 9/2013 | Kawamoto et al. |
| 2014/0045899 | A1 | 2/2014 | Kawamoto et al. |
| 2014/0057892 | A1 | 2/2014 | Kawamoto et al. |
| 2015/0119425 | A1 | 4/2015 | Kawamoto et al. |
| 2015/0141467 | A1 | 5/2015 | Copp et al. |
| 2015/0361043 | A1 | 12/2015 | Lanthier et al. |
| 2016/0009648 | A1 | 1/2016 | Kawamoto et al. |
| 2016/0143891 | A1 | 5/2016 | Shalwitz et al. |
| 2016/0199434 | A1 | 7/2016 | Eubank et al. |
| 2016/0214939 | A1 | 7/2016 | Hanselmann et al. |
| 2016/0339005 | A1 | 11/2016 | Shalwitz et al. |
| 2017/0189387 | A1 | 7/2017 | Kawamoto et al. |
| 2017/0258773 | A1 | 9/2017 | Copp et al. |
| 2017/0362178 | A1 | 12/2017 | Lanthier et al. |
| 2018/0065933 | A1 | 3/2018 | Hanselmann |
| 2018/0092892 | A1 | 4/2018 | Smith et al. |
| 2018/0280365 | A1 | 10/2018 | Copp et al. |
| 2019/0192494 | A1 | 6/2019 | Kawamoto et al. |
| 2020/0345711 | A1 | 11/2020 | Copp et al. |
| 2021/0122715 | A1 | 4/2021 | Lanthier et al. |
| 2021/0137901 | A1 | 5/2021 | Kawamoto et al. |
| 2021/0206721 | A1 | 7/2021 | Ranjan et al. |

FOREIGN PATENT DOCUMENTS

| | | |
|---|---|---|
| CN | 105837502 A | 8/2016 |
| CN | 106146491 A | 11/2016 |
| CN | 111320577 A | 6/2020 |
| EP | 0650960 A1 | 5/1995 |
| EP | 0650961 A1 | 5/1995 |
| EP | 2044005 B1 | 10/2010 |
| EP | 3290404 A1 | 3/2018 |
| EP | 3290404 B1 | 12/2019 |
| JP | H09221476 A | 8/1997 |
| JP | 2001048786 A | 2/2001 |
| JP | 2007194072 A | 8/2007 |
| JP | 2010527378 A | 8/2010 |
| WO | 9622021 A1 | 7/1996 |
| WO | 9744333 A1 | 7/1997 |
| WO | 9741103 A1 | 11/1997 |
| WO | 9948870 A1 | 9/1999 |
| WO | 02074980 A2 | 9/2002 |
| WO | 02074981 A2 | 9/2002 |
| WO | 02083688 A1 | 10/2002 |
| WO | 03028663 A2 | 4/2003 |
| WO | 03032972 A1 | 4/2003 |
| WO | 03049686 A2 | 6/2003 |
| WO | 03053997 A2 | 7/2003 |
| WO | 03097040 A1 | 11/2003 |
| WO | 2004019868 A2 | 3/2004 |
| WO | 2004035812 A2 | 4/2004 |
| WO | 2004048383 A1 | 6/2004 |
| WO | 2004108121 A1 | 12/2004 |
| WO | 2005007192 A2 | 1/2005 |
| WO | 2005115984 A2 | 12/2005 |
| WO | 2005118836 A2 | 12/2005 |
| WO | 2006019831 A1 | 2/2006 |
| WO | 2006030977 A2 | 3/2006 |
| WO | 2006114213 A1 | 11/2006 |
| WO | 2006138511 A2 | 12/2006 |
| WO | 2007038571 A2 | 4/2007 |
| WO | 2007047194 A2 | 4/2007 |
| WO | 2007070359 A2 | 6/2007 |
| WO | 2007082899 A1 | 7/2007 |
| WO | 2007084667 A2 | 7/2007 |
| WO | 2007088571 A2 | 8/2007 |
| WO | 2007103905 A2 | 9/2007 |
| WO | 2007136990 A2 | 11/2007 |
| WO | 2007150011 A2 | 12/2007 |
| WO | 2008002576 A2 | 1/2008 |
| WO | 2008089051 A1 | 7/2008 |
| WO | 2008089052 A2 | 7/2008 |
| WO | 2008130508 A1 | 10/2008 |
| WO | 2008130527 A1 | 10/2008 |
| WO | 2008137060 A1 | 11/2008 |
| WO | 2008141731 A2 | 11/2008 |
| WO | 2008144266 A1 | 11/2008 |
| WO | 2009019656 A1 | 2/2009 |
| WO | 2009020119 A1 | 2/2009 |
| WO | 2009035534 A2 | 3/2009 |
| WO | 2009037570 A2 | 3/2009 |
| WO | 2009039321 A1 | 3/2009 |
| WO | 2009039323 A1 | 3/2009 |
| WO | 2009043093 A1 | 4/2009 |
| WO | 2009049112 A1 | 4/2009 |
| WO | 2009067790 A1 | 6/2009 |
| WO | 2009070644 A1 | 6/2009 |
| WO | 2009073497 A2 | 6/2009 |
| WO | 2009073669 A1 | 6/2009 |
| WO | 2009086044 A1 | 7/2009 |
| WO | 2009086592 A1 | 7/2009 |
| WO | 2009089547 A1 | 7/2009 |
| WO | 2009111337 A1 | 9/2009 |
| WO | 2010029577 A2 | 3/2010 |
| WO | 2010113942 A1 | 10/2010 |
| WO | 2010128355 A2 | 11/2010 |
| WO | 2011057112 A1 | 5/2011 |
| WO | 2012170377 A1 | 12/2012 |
| WO | 2012170439 A1 | 12/2012 |
| WO | 2012170442 A1 | 12/2012 |
| WO | 2013013609 A1 | 1/2013 |
| WO | 2014168986 A1 | 10/2014 |
| WO | 2014200773 A2 | 12/2014 |
| WO | 2015023967 A2 | 2/2015 |
| WO | 2015073779 A1 | 5/2015 |
| WO | 2015112831 A1 | 7/2015 |
| WO | 2016109300 A1 | 7/2016 |
| WO | 2016118858 A1 | 7/2016 |
| WO | 2016153996 A1 | 9/2016 |
| WO | 2016161094 A1 | 10/2016 |

(56) References Cited

FOREIGN PATENT DOCUMENTS

| WO | 2019217550 A1 | 11/2019 |
|---|---|---|
| WO | 2021087144 A1 | 5/2021 |
| WO | 2021188936 A1 | 9/2021 |
| WO | 2021188938 A1 | 9/2021 |
| WO | 2021188944 A1 | 9/2021 |

OTHER PUBLICATIONS

CAS Registry Nos. 1261773-17-4, 1261723-73-2, Chemcats, 2011, (2 pages).
CAS Registry Nos. 1261813-98-2, 1261613-86-8, and 1261518-21-1, Chemcats, 2011, (2 pages).
CAS Registry Nos. 1361609-40-6, 1361556-21-9, 1361555-42-1, 1361544-77-5, 1361480- 63-8, 1361477-92-0, Chemcats, 2012, (6 pages).
CAS Registry Nos. 1361809-77-9, 1361737-20-3, 1361721-11-0, 1361693-45-9, 1361676- 79-0, Chemcats, 2012, (5 pages).
ClinicalTrials.gov, Archive No. NCT01235936, Aug. 30, 2012, retrieved Dec. 1, 2014 from URL: http://clinicaltrials.gov/archive/NCT01235936/2012_09_30, (3 pages).
Decision of the Technical Board of Appeal of the European Patent Office for Case No. T 0777/08 dated May 24, 2011, retrieved Dec. 19, 2017 from URL: https://www.epo.org/boards-of-appeal/decisions/pdf/t080777ex1.pdf (17 pages).
"Akebia Closes $41 Million Series C", Triathlon Medical Ventures, Jun. 4, 2013, retrieved Dec. 1, 2014 from URL: http://www.tmvp.com/news_Akebia_06042013.html, (3 pages).
"Hippuric Acid Sodium Salt", Science Lab.com: Chemicals & Laboratory Equipment, retrieved Mar. 11, 2010 from URL: http://web.archive.org/web/20041107121553/http://sciencelab.com/page/S/PVAR/10415/SLH2620, (1 page).
"International Preliminary Report on Patentability", International Preliminary Report on Patentability, Ch. I, for PCT/US2019/031310 dated Nov. 19, 2020 (6 pages), Nov. 19, 2020.
"International Search Report and Written Opinion", International Search Report and Written Opinion for PCT/US2019/031310 dated Aug. 7, 2019 (10 pages), Aug. 7, 2019.
"SCHEMBL3484399", PubChem, National Center for Biotechnology Information, CID 49848485, Jan. 31, 2011, retrieved Mar. 15, 2016 from URL: https://pubchem.ncbi.nlm.nih.gov/compound/49848485, (13 pages).
"XEADCOHJERWFOI-UHFFFAOYSA-M", PubChem, National Center for Biotechnology Information, CID 71491828, Jun. 10, 2013, retrieved Mar. 21, 2016 from URL: https://pubchem.ncbi.nlm.nih.gov/compound/71491828, (12 pages).
Acker, Till , et al., "Genetic evidence for a tumor suppressor role of HIF-2α", Cancer Cell, vol. 8, No. 2, Aug. 2005, pp. 131-141, DOI: 10.1016/j.ccr.2005.07.003, (11 pages).
Alesso, Sonia M, et al., "Improving resins for solid phase synthesis: incorporation of 1-[2-(2-methoxyethoxy)ethoxy]-4-vinyl-benzene", Tetrahedron, vol. 59, No. 36, Sep. 1, 2003, pp. 7163-7169, DOI: 10.1016/S0040-4020(03)01100-1, (7 pages).
Altschul, Stephen F, et al., "Gapped BLAST and PSI-BLAST: a new generation of protein database search programs", Nucleic Acids Research, vol. 25, No. 17, Sep. 1, 1997, pp. 3389-3402, DOI: 10.1093/nar/25.17.3389, (14 pages).
Anderson, Neal G, "Chapter 12—Crystallization and Purification", Practical Process Research and Development (Second Edition), 2012, pp. 329-364, DOI: 10.1016/B978-0-12-386537-3.00012-5, (38 pages).
Anderson, Wayne K., et al., "Antileukemic activity of derivatives of 1,2-dimethyl-3,4-bis(hydroxymethyl)-5-phenylpyrrole bis(N-methylcarbamate)", Journal of Medicinal Chemistry, vol. 22, No. 8, 1979, pp. 977-980, DOI: 10.1021/jm00194a018, (4 pages).
Annex, Brian H., et al., "Growth factor-induced therapeutic angiogenesis in the heart: protein therapy", Cardiovascular Research, vol. 65, No. 3, Feb. 2005, pp. 649-655, DOI: 10.1016/j.cardiores.2004.09.004, (7 pages).

Ardelt, Agnieszka A., et al., "Estradiol Regulates Angiopoietin-1 mRNA Expression Through Estrogen Receptor-α in a Rodent Experimental Stroke Model", Stroke, vol. 36, No. 2, Feb. 2005, pp. 337-341, DOI: 10.1161/01.STR.0000153795.38388.72, (6 pages).
Auerbach, Robert , et al., "Angiogenesis Assays: A Critical Overview", Clinical Chemistry, vol. 49, No. 1, 2003, pp. 32-40, DOI: 10.1373/49.1.32, (9 pages).
Barany, George , et al., "Solid-phase peptide synthesis: a silver anniversary report", Chemical Biology & Drug Design, vol. 30, No. 6, 1987, pp. 705-739, DOI: 10.1111/j.1399-3011.1987.tb03385.x, (35 pages).
Bartlett, Paul A., et al., "CAVEAT: a program to facilitate the design of organic molecules", Molecular Recognition in Chemical and Biological Problems, Special Pub., Royal Society of Chemistry, 1989, pp. 182-196 (15 pages).
Böhm, Hans-Joachim , "The computer program LUDI: A new method for the de novo design of enzyme inhibitors", Journal of Computer-Aided Molecular Design, vol. 6, No. 1, 1992, pp. 61-78, DOI: 10.1007/BF00124387, (18 pages).
Branden, Carl Ivar, et al., "Introduction to Protein Structure, Second Edition", Garland Science, 1998, pp. 374-375, (4 pages).
Brittain, Harry G., et al., "Polymorphism in Pharmaceutical Solids, Second Edition", Drugs and Pharmaceutical Sciences, vol. 192, 2009, pp. 333-335, (7 pages).
Burger, Alfred , "Isosterism and bioisosterism in drug design", Progress in Drug Research, vol. 37, 1991, pp. 287-371, DOI: 10.1007/978-3-0348-7139-6_7, (85 pages).
Bussolino, Federico , et al., "Molecular mechanisms of blood vessel formation", Trends in Biochemical Sciences, vol. 22, No. 7, Jul. 1997, pp. 251-256, DOI: 10.1016/s0968-0004(97)01074-8, (6 pages).
Byrn, Stephen , et al., "Pharmaceutical Solids: A Strategic Approach to Regulatory Considerations", Pharmaceutical Research, vol. 12, No. 7, 1995, pp. 945-954, DOI: 10.1023/a:1016241927429, (10 pages).
Carey, Francis A., "", Organic Chemistry, Sixth Edition, McGraw Hill, 2006, Chapter 1, pp. 9, Chapter 19, pp. 839-840, and Chapter 27, pp. 1182-1183, (12 pages).
Catrina, Sergiu-Bogdan , et al., "Hyperglycemia Regulates Hypoxia-Inducible Factor-1a Protein Stability and Function", Diabetes, vol. 53, No. 12, 2004, pp. 3226-3232, DOI: 10.2337/diabetes.53.12.3226, (7 pages).
Cheeseright, Tim , "The Identification of Bioisosteres as Drug Development Candidates", Innovations in Pharmaceutical Technology, 2009, (4 pages).
Cherng, Yie-Jia , "Synthesis of substituted pyridines by the reactions of halopyridines with sulfur, oxygen and carbon nucleophiles under focused microwave irradiation", Tetrahedron, vol. 58, No. 24, Jun. 10, 2002, pp. 4931-4935, DOI: 10.1016/S0040-4020(02)00424-6, (5 pages).
Costello, Leslie C., et al., "Evidence for Changes in RREB-1, ZIP3, and Zinc in the Early Development of Pancreatic Adenocarcinoma", Journal of Gastrointestinal Cancer, vol. 43, No. 4, 2012, pp. 570-578, DOI: 10.1007/s12029-012-9378-1, (9 pages).
Cousins, Scott W., "Intravitreal Anti-VEGF and Anti-PDGF Combination Therapy", Retina Today, Oct. 2009, Retrieved from URL: http://retinatoday.com/2009/10/1009_12.php, (2 pages).
Cunliffe, C. Jane , et al., "Novel inhibitors of prolyl 4-hydroxylase. 3. Inhibition by the substrate analog N-oxaloglycine and its derivatives", Journal of Medicinal Chemistry, vol. 35, No. 14, 1992, pp. 2652-2658, DOI: 10.1021/jm00092a016, (7 pages).
Demetriades, Marina , et al., "Dynamic Combinatorial Chemistry Employing Boronic Acids/Boronate Esters Leads to Potent Oxygenase Inhibitors", Angewandte Chemie, International Edition , vol. 51, No. 27, Jul. 2, 2012, pp. 6672-6675, DOI: 10.1002/anie.201202000, (4 pages).
Dranoff, Glenn , "GM-CSF-secreting melanoma vaccines", Oncogene, vol. 22, 2003, pp. 3188-3192, DOI: 10.1038/sj.onc.1206459, (5 pages).
Elson, David A., et al., "Induction of hypervascularity without leakage or inflammation in transgenic mice overexpressing hypoxia-inducible factor-1α", Genes & Development, vol. 15, 2001, pp. 2520-2532, DOI: 10.1101/gad.914801, (13 pages).
Elvidge, Gareth P., et al., "Concordant Regulation of Gene Expression by Hypoxia and 2-Oxoglutarate-dependent Dioxygenase Inhi-

(56) References Cited

OTHER PUBLICATIONS bition", Journal of Biological Chemistry, vol. 281, No. 22, Jun. 2006, pp. 15215-15226, DOI: 10.1074/jbc.M511408200, (13 pages).
Enoch, Stuart, et al., "ABC of wound healing: Non-surgical and drug treatments", BMJ, vol. 332, No. 7546, 2006, pp. 900-903, DOI: 10.1074/jbc.M511408200, (4 pages).
Favier, Judith, et al., "HIF2α reduces growth rate but promotes angiogenesis in a mouse model of neuroblastoma", BMC Cancer, vol. 7, Article No. 139, 2007, DOI: 10.1186/1471-2407-7-139, (10 pages).
Flower, Darren R, et al., "Modelling G-protein-coupled receptors for drug design", Biochimica et Biophysica Acta (BBA)—Reviews on Biomembranes, vol. 1422, No. 3, Nov. 16, 1999, pp. 207-234, DOI: 10.1016/s0304-4157(99)00006-4, (28 pages).
Folkman, Judah, "Chapter 10—Tumor Angiogenesis", The Molecular Basis of Cancer, 1995, pp. 206-232, (29 pages).
Franklin, Trevor J, et al., "Approaches to the design of anti-fibrotic drugs", Biochemical Society Transactions, vol. 19, No. 4, Nov. 1991, pp. 812-815, DOI: 10.1042/bst0190812, (4 pages).
Gaunt, Matthew J, et al., "Rational Design of Benzyl-Type Protecting Groups Allows Sequential Deprotection of Hydroxyl Groups by Catalytic Hydrogenolysis", Journal of Organic Chemistry, vol. 63, No. 13, 1998, pp. 4172-4173, DOI: 10.1021/JO980823V, (2 pages).
Gaunt, Matthew J, et al., "Rational Design of Benzyl-Type Protecting Groups Allows Sequential Deprotection of Hydroxyl Groups by Catalytic Hydrogenolysis", Journal of Organic Chemistry, vol. 63, No. 13, 1998, pp. 4172-4173, DOI: 10.1021/JO980823V, Supplementary Materials (14 pages).
Gavhane, Y. N., et al., "Solid Tumors: Facts, Challenges and Solutions", International Journal of Pharma Sciences and Research, vol. 2, No. 1, 2011, pp. 1-12, (12 pages).
Goodford, P. J., et al., "A computational procedure for determining energetically favorable binding sites on biologically important macromolecules", Journal of Medicinal Chemistry, vol. 28, No. 7, 1985, pp. 849-857, DOI: 10.1021/jm00145a002m (9 pages).
Goodsell, David S., et al., "Automated docking of substrates to proteins by simulated annealing", Proteins, vol. 8, No. 3, 1990, pp. 195-202, DOI: 10.1002/prot.340080302, (8 pages).
Greer, Samantha N, et al., "The updated biology of hypoxia-inducible factor", The EMBO Journal, vol. 31, No. 11, May 30, 2012, pp. 2448-2460, DOI: 10.1038/emboj.2012.125, (13 pages).
Hardcastle, Ian R., et al., "Discovery of Potent Chromen-4-one Inhibitors of the DNA-Dependent Protein Kinase (DNA-PK) Using a Small-Molecule Library Approach", Journal of Medicinal Chemistry, vol. 48, No. 24, 2005, pp. 7829-7846, DOI: 10.1021/jm050444b, (18 pages).
Hoeksema, H., et al., "Structure of rubradirin", Journal of the American Chemical Society, vol. 104, No. 19, 1982, pp. 5173-5181, DOI: 10.1021/ja00383a030, (9 pages).
Hu, Cheng-Jun, et al., "Differential Roles of Hypoxia-Inducible Factor 1α (HIF-1α) and HIF-2α in Hypoxic Gene Regulation", Molecular and Cellular Biology, vol. 23, No. 24, 2003, pp. 9361-9374, DOI: 10.1128/MCB.23.24.9361-9374.2003, (14 pages).
Ingersoll, A. W., et al., "Hippuric Acid", Organic Synthesis, CV 2, 328, Retrieved on Mar. 11, 2010 from the Internet at <http://web.archive.org/web/20020724135719/http://www.orgsyn.org/orgsyn/orgsyn/prepContent.asp?prep=cv2p0328>, (4 pages).
Ivan, Mircea, et al., "Biochemical purification and pharmacological inhibition of a mammalian prolyl hydroxylase acting on hypoxia-inducible factor", PNAS, vol. 99, No. 21, Sep. 26, 2002, pp. 13459-13464, DOI: 10.1073/pnas.192342099, (6 pages).
Ivan, Mircea, et al., "HIFα Targeted for VHL-Mediated Destruction by Proline Hydroxylation: Implications for O2 Sensing", Science, vol. 292, No. 5516, Apr. 5, 2001, pp. 464-468, DOI: 10.1126/science.1059817, (5 pages).
Ivanisevic, Igor, et al., "Uses of X-Ray Powder Diffraction In the Pharmaceutical Industry", Pharmaceutical Formulation and Quality, 2010, DOI: 10.1002/9780470571224.pse414, (4 pages).
Iyoda, Masahiko, et al., "Homocoupling of Aryl Halides Using Nickel(II) Complex and Zinc in the Presence of Et4NI. An Efficient Method for the Synthesis of Biaryls and Bipyridines", Bulletin of the Chemical Society of Japan, vol. 63, No. 1, 1990, pp. 80-87, DOI: 10.1246/bcsj.63.80, (8 pages).
Jaakkola, Panu, et al., "Targeting of HIF-α to the von Hippel-Lindau Ubiquitylation Complex by O2-Regulated Prolyl Hydroxylation", Science, vol. 292, No. 5516, Apr. 5, 2001, pp. 468-472, DOI: 10.1126/science.1059796, (5 pages).
Jones, Gareth, et al., "Molecular recognition of receptor sites using a genetic algorithm with a description of desolvation", Journal of Molecular Biology, vol. 245, No. 1, 1995, pp. 43-53, DOI: 10.1016/s0022-2836(95)80037-9, (11 pages).
Kaelin, William G., "Proline hydroxylation and gene expression", Annual Review of Biochemistry, vol. 74, 2005, pp. 115-128, DOI: 10.1146/annurev.biochem.74.082803.133142, (14 pages).
Karuppagounder, Saravanan S, et al., "Hypoxia-Inducible Factor Prolyl Hydroxylase Inhibition: Robust New Target or Another Big Bust for Stroke Therapeutics?", Journal of Cerebral Blood Flow & Metabolism, vol. 32, No. 7, 2012, pp. 1347-1361, DOI: 10.1038/jcbfm.2012.28, (14 pages).
Kawashima, Yoichiro, et al., "Suppressive Effect of Quinolinic Acid and Hippuric Acid on Bone Marrow Erythroid Growth and Lymphocyte Blast Formation in Uremia", Advances in Experimental Medicine and Biology, vol. 223, 1987, pp. 69-72, DOI: 10.1007/978-1-4684-5445-1_9, (5 pages).
Ke, Qingdong, et al., "Hypoxia-Inducible Factor-1 (HIF-1)", Molecular Pharmacology, vol. 70, No. 5, Nov. 2006, pp. 1469-1480, DOI: 10.1124/mol.106.027029, (12 pages).
Khandhadia, Sam, et al., "Age-Related Macular Degeneration", Neurodegenerative Diseases, Landes Bioscience and Springer Science+Business Media, 2012, pp. 15-36, (22 pages).
Kietzmann, Thomas, et al., "Perivenous expression of the mRNA of the three hypoxia-inducible factor α-subunits, HIF1α, HIF2α and HIF3α, in rat liver", Biochemical Journal, vol. 354, No. 3, Mar. 2001, pp. 531-537, DOI: 10.1042/bj3540531, (7 pages).
Kim, so Yeon, et al., "Recent Advances in Developing Inhibitors for Hypoxia-Inducible Factor Prolyl Hydroxylases and Their Therapeutic Implications", Molecules, vol. 20, No. 11, 2015, pp. 20551-20568, DOI: 10.3390/molecules201119717, (18 pages).
Kirwan, D.J., et al., "11-Crystallization in the pharmaceutical and bioprocessing industries", Handbook of Industrial Crystallization (Second Edition), 2002, pp. 249-266, DOI: 10.1016/B978-075067012-8/50013-6, (20 pages).
Krantz, Sanford B, "Erythropoietin", Blood, vol. 77, No. 3, Feb. 1, 1991, pp. 419-434, DOI: 10.1182/blood.V77.3.419.419, (16 pages).
Kuntz, Irwin D., et al., "A geometric approach to macromolecule-ligand interactions", Journal of Molecular Biology, vol. 161, No. 2, Oct. 25, 1982, pp. 269-288, DOI: 10.1016/0022-2836(82)90153-x, (20 pages).
Kurti, Laszlo, et al., "Strategic Applications of Named Reactions in Organic Synthesis", Elsevier, 2005, pp. 448-449, (4 pages).
Langsetmo, Ingrid, et al., "Inhibition of HIF-Prolyl Hydroxylases with FG-4539 IS Neuroprotective in a Mouse Model of Permanent Focal Ischemia", International Stroke Conference, Kissimmee, Florida, Presentation No. 427, 2006, Abstract (1 page).
Lee, Cheolju, et al., "Structure of Human FIH-1 Reveals a Unique Active Site Pocket and Interaction Sites for HIF-1 and von Hippel-Lindau", Enzyme Catalysis and Regulation, vol. 278, No. 9, Feb. 2003, pp. 7558-7563, DOI: 10.1074/jbc.M210385200, (7 pages).
Li, Jian, et al., "PR39, a peptide regulator of angiogenesis", Nature Medicine, vol. 6, No. 1, 2000, pp. 49-55, DOI: 10.1038/71527, (7 pages).
Lima, Lidia Moreira, et al., "Bioisosterism: A Useful Strategy for Molecular Modification and Drug Design", Current Medicinal Chemistry, vol. 12, No. 1, 2005, pp. 23-49, DOI: 10.2174/0929867053363540, (27 pages).
Liu, Quanyan, et al., "Hypoxia induces genomic DNA demethylation through the activation of HIF-1α and transcriptional upregulation of MAT2A in hepatoma cells", Molecular Cancer Therapeutics, vol. 10, No. 6, Jun. 1, 2011, pp. 1113-1123, Doi: 10.1158/1535-7163. MCT-10-1010, (12 pages).
Mancini, Donna M, et al., "Effect of Erythropoietin on Exercise Capacity in Patients With Moderate to Severe Chronic Heart

(56) References Cited

OTHER PUBLICATIONS

Failure", Circulation, vol. 107, No. 2, 2002, pp. 294-299, DOI: 10.1161/01.CIR.0000044914.42696.6A, (7 pages).
McDonough, Michael A., et al., "Cellular oxygen sensing: Crystal structure of hypoxia-inducible factor prolyl hydroxylase (PHD2)", PNAS, vol. 103, No. 26, Jun. 27, 2006, pp. 9814-9819, DOI: 10.1073/pnas.0601283103, (6 pages).
Miranker, Andrew, et al., "Functionality maps of binding sites: A multiple copy simultaneous search method", Proteins: Structure, Function and Genetics, vol. 11, No. 1, Sep. 1991, pp. 29-34, DOI: 10.1002/prot.340110104, (6 pages).
Morissette, Sherry L., et al., "High-throughput crystallization: polymorphs, salts, co- crystals and solvates of pharmaceutical solids", Advanced Drug Delivery Reviews, vol. 56, No. 3, Feb. 23, 2004, pp. 275-300, DOI: 10.1016/j.addr.2003.10.020, (26 pages).
Moss, G.P., et al., "Glossary of class names of organic compounds and reactivity intermediates based on structure (IUPAC Recommendations 1995)", Pure and Applied Chemistry, vol. 67, Nos. 8/9, 1995, pp. 1307-1375, DOI: 10.1351/pac199567081307, (69 pages).
Nguyen, Louis L., et al., "Cellular interactions in vascular growth and differentiation", International Review of Cytology, vol. 204, 2001, pp. 1-48, DOI: 10.1016/s0074-7696(01)04002-5, (48 pages).
Nielsen, Dorte Lisbet, "Antiangiogenic therapy for breast cancer", Breast Cancer Research, vol. 12, Article No. 209, 2010, DOI: 10.1186/bcr2642, (16 pages).
Nishibata, Yoshihiko, et al., "Automatic creation of drug candidate structures based on receptor structure. Starting point for artificial lead generation.", Tetrahedron, vol. 47, No. 43, Nov. 4, 1991, pp. 8985-8990, DOI: 10.1016/S0040-4020(01)86503-0, (6 pages).
Nowak, Jerzy Z, "Age-related macular degeneration (AMD): pathogenesis and therapy", Pharmacological Reports, vol. 58, 2006, pp. 353-363, (11 pages).
O'Reilly, Michael S., et al., "Angiostatin: A novel angiogenesis inhibitor that mediates the suppression of metastases by a lewis lung carcinoma", Cell, vol. 79, No. 2, 1994, pp. 315-328, DOI: 10.1016/0092-8674(94)90200-3, (14 pages).
O'reilly, Michael S., "Endostatin: An Endogenous Inhibitor of Angiogenesis and Tumor Growth", Cell, vol. 88, No. 2, 1997, pp. 277-285, DOI: 10.1016/S0092-8674(00)81848-6, (9 pages).
Pasqualetti, P., et al., "Circadian rhythm of serum erythropoietin in myelodysplastic syndromes", European Review for Medical and Pharmacological Sciences, vol. 4, 2000, pp. 111-115 (5 pages).
Pergola, Pablo E., et al., "Vadadustat, a novel oral HIF stabilizer, provides effective anemia treatment in nondialysis-dependent chronic kidney disease", Kidney International, vol. 90, No. 5, Nov. 2016, pp. 1115-1122, DOI: 10.1016/j.kint.2016.07.019, (8 pages).
Peyssonnaux, Carole, et al., "HIF-1α expression regulates the bactericidal capacity of phagocytes", The Journal of Clinical Investigation, vol. 115, No. 7, Jul. 2005, pp. 1806-1815, DOI: 10.1172/JCI23865, (10 pages).
Piyamongkol, Sirivipa, et al., "Amido-3-hydroxypyridin-4-ones as Iron(III) Ligands", Chemistry A European Journal, vol. 16, No. 21, Jun. 1, 2010, pp. 6374-6381, DOI: 10.1002/chem.200902455, (8 pages).
Piyamongkol, Sirivipa, et al., "Amido-3-hydroxypyridin-4-ones as Iron(III) Ligands", Chemistry A European Journal, vol. 16, No. 21, Jun. 1, 2010, pp. 6374-6381, DOI: 10.1002/chem.200902455, Supporting Information (53 pages).
Prabhakar, Nanduri R., et al., "Adaptive and Maladaptive Cardiorespiratory Responses to Continuous and Intermittent Hypoxia Mediated by Hypoxia-Inducible Factors 1 and 2", Physiological Reviews, vol. 92, No. 3, Jul. 2012, pp. 967-1003, DOI: 10.1152/physrev.00030.2011, Author Manuscript (6 pages).
Qian, Jia Qi, et al., "A Randomized, Double-Bind, Placebo Controlled Trial FG-4592 for Correction of Anemia in Subjects with Chronic Kidney Disease in China", Journal of the American Society of Nephrology, vol. 24, 2013, Oral Abstract FR-OR011 (1 page).
Qunibi, Wajeh Y., et al., "A randomized controlled trial comparing intravenous ferric carboxymaltose with oral iron for treatment of iron deficiency anaemia of non-dialysis-dependent chronic kidney disease patients", Nephrology Dialysis Transplantation, vol. 26, No. 5, May 2011, pp. 1599-1607, DOI: 10.1093/ndt/gfq613, (9 pages).
Rahtu-Korpela, Lea, et al., "HIF Prolyl 4-Hydroxylase-2 Inhibition Improves Glucose and Lipid Metabolism and Protects Against Obesity and Metabolic Dysfunction", Diabetes, vol. 63, No. 10, 2014, pp. 3324-3333, DOI: 10.2337/db14-0472, (10 pages).
Rankin, Erinn B., et al., "Hypoxia-inducible factor-2 (HIF-2) regulates hepatic erythropoietin in vivo", The Journal of Clinical Investigation, vol. 117, No. 4, Apr. 2007, pp. 1068-1077, DOI: 10.1172/JCI30117, (10 pages).
Ratcliffe, Peter J., "HIF-1 and HIF-2: working alone or together in hypoxia?", The Journal of Clinical Investigation, vol. 117, No. 4, Apr. 2007, 862-865, DOI: 10.1172/JCI31750, (4 pages).
Redondo, Pedro, et al., "Vascular endothelial growth factor (VEGF) and melanoma. N-acetylcysteine downregulates VEGF production in vitro", Cytokine, vol. 12, No. 4, Apr. 2000, pp. 374-378, DOI: 10.1006/cyto.1999.0566, (5 pages).
Roda, Julie M., et al., "Stabilization of HIF-2α Induces sVEGFR-1 Production from Tumor-Associated Macrophages and Decreases Tumor Growth in a Murine Melanoma Model", The Journal of Immunology, vol. 189, No. 6, Sep. 15, 2012, pp. 3168-3177, DOI: 10.4049/jimmunol.1103817, Author Manuscript (23 pages).
Schelhaas, Michael, et al., "Protecting Group Strategies in Organic Synthesis", Angewandte Chemie, International Edition, vol. 35, No. 18, Oct. 1, 1996, pp. 2056-2083, DOI: 10.1002/anie.199620561, (27 pages).
Schöneberg, Torsten, et al., "Structural basis of G protein-coupled receptor function", Molecular and Cellular Endocrinology, vol. 151, No. 1-2, May 25, 1999, pp. 181-193, 10.1016/S0303-7207(99)00017-9, (13 pages).
Semenza, Gregg L, "Regulation of Erythropoiesis by the Hypoxia-Inducible Factor Pathway: Effects of Genetic and Pharmacological Perturbations", Hematology/Oncology Clinic of North America, vol. 8, No. 5, Oct. 1994, pp. 863-884, (22 pages).
Semenza, Gregg L., et al., "HIF-1 and human disease: one highly involved factor", Genes & Development, vol. 14, No. 16, 2000, pp. 1983-1991, DOI: 10.1101/gad.14.16.1983, (10 pages).
Semenza, Gregg L., et al., "Signal transduction to hypoxia-inducible factor 1", Biochemical Pharmacology, vol. 64, No. 5-6, Sep. 2002, pp. 993-998, DOI: 10.1016/s0006-2952(02)01168-1, (6 pages).
Semenza, Gregg L., et al., "Transcriptional regulation of genes encoding glycolytic enzymes by hypoxia-inducible factor 1", The Journal of Biological Chemistry, vol. 269, No. 38, Sep. 23, 1994, pp. 23757-23763, (7 pages).
Sexton, Patrick M, et al., "Recent advances in our understanding of peptide hormone receptors and RAMPS", Current Opinions in Drug Discovery & Development, vol. 2, No. 5, 1999, pp. 440-448, (9 pages).
Sheehan, John T, "3-Hydroxypicolinic Acid and Some of Its Derivatives", The Journal of Organic Chemistry, vol. 31, No. 2, 1966, pp. 636-638, DOI; 10.1021/jo01340a533, (5 pages).
Siddiq, Ambreena, et al., "Hypoxia-inducible Factor Prolyl 4-Hydroxylase Inhibition. A target for neuroprotection in the central nervous system", Journal of Biological Chemistry, vol. 280, No. 50, Dec. 2005, pp. 41732-41743, DOI: 10.1074/jbc.M504963200, (13 pages).
Sowter, Heidi M., et al., "Predominant Role of Hypoxia-Inducible Transcription Factor (Hif)-1α versus Hif-2α in Regulation of the Transcriptional Response to Hypoxia", Cancer Research, vol. 63, No. 19, Oct. 1, 2003, pp. 6130-6134, (8 pages).
Sporn, Michael B., et al., "Chemoprevention of cancer", Carcinogenesis, vol. 21, No. 3, Mar. 2000, pp. 525-530, DOI: 10.1093/carcin/21.3.525, (6 pages).
Stille, John K., et al., "The Palladium-Catalyzed Cross-Coupling Reactions of Organotin Reagents with Organic Electrophiles", Angewandte Chemie, International Edition, vol. 25, No. 6, Jun. 1986, pp. 508-524, DOI: 10.1002/anie.198605081, (18 pages).
Stohlawetz, Petra Jilma, et al., "Effects of erythropoietin on platelet reactivity and thrombopoiesis in humans", Blood, vol. 95, No. 9, May 1, 2000, pp. 2983-2989 (7 pages).
Sutter, Carrie Hayes, et al., "Hypoxia-inducible factor 1α protein expression is controlled by oxygen-regulated ubiquitination that is

(56) References Cited

OTHER PUBLICATIONS disrupted by deletions and missense mutations", PNAS, vol. 97, No. 9, Apr. 11, 2000, pp. 4748-4753, DOI: 10.1073/pnas.080072497, (6 pages).
Teicher, Beverly A., et al., "Potentiation of cytotoxic cancer therapies by TNP-470 alone and with other anti-angiogenic agents", International Journal of Cancer, vol. 57, No. 6, Jun. 15, 1994, pp. 920-925, DOI: 10.1002/ijc.2910570624, (6 pages).
Thoppil, Roslin J, et al., "Terpenoids as potential chemopreventive and therapeutic agents in liver cancer", World Journal of Hepatology, vol. 3, No. 9, 2011, pp. 228-249, DOI: 10.4254/wjh.v3.i9.228, (22 pages).
Thornber, C. W., et al., "Isosterism and molecular modification in drug design", Chemical Society Reviews, No. 8, 1979, 563-580, DOI: 10.1039/CS9790800563, (18 pages).
Tzschucke, Carl Christoph, et al., "Fluorous-Silica-Supported Perfluoro-Tagged Palladium Complexes Catalyze Suzuki Couplings in Water", Helvetica Chima Acta, vol. 87, No. 11, Nov. 2004, pp. 2882-2889, DOI: 10.1002/hlca.200490260, (8 pages).
Ullman, F., et al., "Ueber Synthesen in der Biphenyireihe", Ber. Deutsch. Chem. Ges., 1901, pp. 2174, (12 pages).
Variankaval, Narayan, et al., "From form to function: Crystallization of active pharmaceutical ingredients", AIChE Journal, vol. 54, No. 7, Jul. 2008, pp. 1682-1688, DOI: 10.1002/aic.11555, (7 pages).
Vickerstaffe, Emma, et al., "Fully Automated Polymer-Assisted Synthesis of 1,5-Biaryl Pyrazoles", Journal of Combinatorial Chemistry, vol. 6, 2004, pp. 332-339, DOI: 10.1021/cc049977g, (8 pages).
Vincent, Karen A., et al., "Angiogenesis Is Induced in a Rabbit Model of Hindlimb Ischemia by Naked DNA Encoding an HIF-1α/VP16 Hybrid Transcription Factor", Circulation, vol. 102, No. 18, Oct. 31, 2000, pp. 2255-2261, DOI: 10.1161/01.cir.102.18.2255, (7 pages).
Vippagunta, Sudha R., et al., "Crystalline solids", Advanced Drug Delivery Reviews, vol. 48, No. 1, May 16, 2001, pp. 3-26, DOI: 10.1016/S0169-409X(01)00097-7, (23 pages).
Wade, L. G., et al., "Organic Chemistry", Wade et al., Organic Chemistry, Sixth Edition, 2005, pp. 780-781, (5 pages).
Warnecke, Christina, et al., "Activation of the hypoxia-inducible factor-pathway and stimulation of angiogenesis by application of prolyl hydroxylase inhibitors", The FASEB Journal, vol. 17, No. 9, 2003, pp. 1186-1188, DOI: 10.1096/fj.02-1062fje, (23 pages).
Warshakoon, Namal C., et al., "Design and synthesis of substituted pyridine derivatives as HIF-1α prolyl hydroxylase inhibitors", Bioorganic & Medicinal Chemistry Letters, vol. 16, No. 21, Nov. 1, 2006, pp. 5616-5620, DOI: 10.1016/j.bmcl.2006.08.026, (5 pages).
Wax, Stephen D., et al., "SM-20 is a novel 40-kd protein whose expression in the arterial wall is restricted to smooth muscle", Laboratory Investigation, vol. 74, No. 4, 1996, pp. 797-808, (12 pages).
Weidner, Noel, et al., "Tumor Angiogenesis and Metastasis—Correlation in Invasive Breast Carcinoma", The New England Journal of Medicine, vol. 324, No. 1, pp. 1-8, DOI: 10.1056/NEJM199101033240101, (111 pages).
Wiesener, Michael S., et al., "Widespread hypoxia-inducible expression of HIF-2alpha in distinct cell populations of different organs", The FASEB Journal, vol. 17, No. 2, 2003, pp. 271-273, DOI: 10.1096/fj.02-0445fje, (22 pages).
Wright, Gary, et al., "Activation of the Prolyl Hydroxylase Oxygen-sensor Results in Induction of GLUT1, Heme Oxygenase-1, and Nitric-oxide Synthase Proteins and Confers Protection from Metabolic Inhibition to Cardiomyocytes", Journal of Biological Chemistry, vol. 278, No. 22, May 2003, pp. 20235-20239, DOI: 10.1074/jbc.M301391200, (5 pages).
Wu, Florence T.H., et al., "A systems biology perspective on sVEGFR1: its biological function, pathogenic role and therapeutic use", Journal of Cellular and Molecular Medicine, vol. 14, No. 3, Apr. 21, 2010, pp. 528-552, DOI: 10.1111/j.1582-4934.2009.00941.x, (25 pages).
Yang, Linlin, et al., "Desmoplakin acts as a tumor suppressor by inhibition of the Wnt/β-catenin signaling pathway in human lung cancer", Carcinogenesis, vol. 33, No. 10, Oct. 2012, pp. 1863-1870, DOI: 10.1093/carcin/bgs226, (8 pages).

* cited by examiner

PROCESS FOR PREPARING 2-[[5-(3-CHLOROPHENYL)-3-HYDROXY-PYRIDINE-2-CARBONYL] AMINO] ACETIC ACID

CROSS-REFERENCE TO RELATED APPLICATION

The present application is a divisional of U.S. patent application Ser. No. 17/053,614, filed Nov. 6, 2020, which is a 35 U.S.C § 371 National Stage Application of International Application No. PCT/US2019/031310, filed on May 8, 2019, which claims benefit of U.S. Provisional Application No. 62/669,135, filed May 9, 2018, each of which is hereby incorporated by reference in its entirety.

FIELD

The invention relates generally to synthetic methods and chemical compositions and more specifically to processes and intermediates thereof useful in preparation and manufacturing of vadadustat (2-[[5-(3-chlorophenyl)-3-hydroxypyridine-2-carbonyl]amino]acetic acid).

BACKGROUND

Vadadustat is a titratable, oral hypoxia-inducible factor prolyl hydroxylase inhibitor that induces endogenous erythropoietin synthesis and enhances iron mobilization. While methods for synthesis of vadadustat have been described, there remains a need for improved methods to manufacture highly pure vadadustat or a pharmaceutically acceptable salt thereof substantially free of the impurities.

SUMMARY

The present invention is based, in part, on the surprising discovery that highly pure vadadustat or a pharmaceutically acceptable salt thereof, which is substantially free of impurities can be manufactured using the methods and compositions described herein.

Disclosed herein are methods and processes of preparing vadadustat and pharmaceutically acceptable salts thereof, and intermediates and their salts useful for the synthesis of vadadustat.

In one aspect, disclosed herein is a process for preparing a compound of Formula (8), (8)

[chemical structure]

or a salt thereof, comprising: contacting a compound of Formula (I) or a salt thereof, (I)

[chemical structure]

wherein: $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl, with a hydrolyzing agent.

In another aspect, disclosed herein is a compound of Formula (I):

(I)

[chemical structure]

or a salt thereof, wherein: $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl.

In another aspect, disclosed herein is a composition comprising:
a) 80% or more of a compound of Formula (I) or a salt thereof, (I)

[chemical structure]

wherein each of $R^1$ and $R^2$ is independently as defined herein; and
b) 20% or less of a compound of Formula (IV) or a salt thereof,

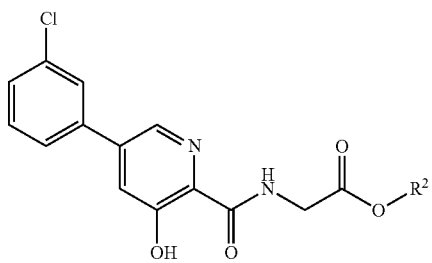

(IV)

wherein R¹ is as defined herein, and wherein the combined amount of the compound of Formula (I) or a salt thereof and the compound of Formula (IV) or a salt thereof is between about 99% and about 100%.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

All temperatures are in degrees Celsius (° C.) unless otherwise specified.

Unless noted otherwise, all purity and related numeric values (%) are as measured by HPLC.

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range.

As used in the specification and appended claims, unless specified to the contrary, the following terms have the meaning indicated below.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

The compounds disclosed herein may contain one or more asymmetric centers and may thus give rise to enantiomers, diastereomers, and other stereoisomeric forms that may be defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

"Amino" refers to the —NH2 radical.

"Alkyl" refers to a straight or branched hydrocarbon chain radical consisting solely of carbon and hydrogen atoms, containing no unsaturation, having from one to fifteen carbon atoms (e.g., $C_{1-15}$ alkyl). In certain embodiments, an alkyl comprises one to thirteen carbon atoms (e.g., $C_{1-13}$ alkyl). In certain embodiments, an alkyl comprises one to ten carbon atoms (e.g., $C_{1-10}$ alkyl). In certain embodiments, an alkyl comprises one to eight carbon atoms (e.g., $C_{1-8}$ alkyl). In other embodiments, an alkyl comprises one to five carbon atoms (e.g., $C_{1-5}$ alkyl). In other embodiments, an alkyl comprises one to four carbon atoms (e.g., $C_{1-4}$ alkyl). In other embodiments, an alkyl comprises one to three carbon atoms (e.g., $C_{1-3}$ alkyl). In other embodiments, an alkyl comprises one to two carbon atoms (e.g., $C_{1-2}$ alkyl). In other embodiments, an alkyl comprises one carbon atom (e.g., $C_1$ alkyl). In other embodiments, an alkyl comprises five to fifteen carbon atoms (e.g., $C_{5-15}$ alkyl). In other embodiments, an alkyl comprises five to ten carbon atoms (e.g., $C_{5-10}$ alkyl). In other embodiments, an alkyl comprises five to eight carbon atoms (e.g., $C_{5-8}$ alkyl). In other embodiments, an alkyl comprises two to five carbon atoms (e.g., $C_{2-5}$ alkyl). In other embodiments, an alkyl comprises three to five carbon atoms (e.g., $C_{3-5}$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1- dimethylethyl (tert-butyl), 1-pentyl (n-pentyl). The alkyl is attached to the rest of the molecule by a single bond.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Halo" or "halogen" refers to bromo, chloro, fluoro or iodo substituents.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

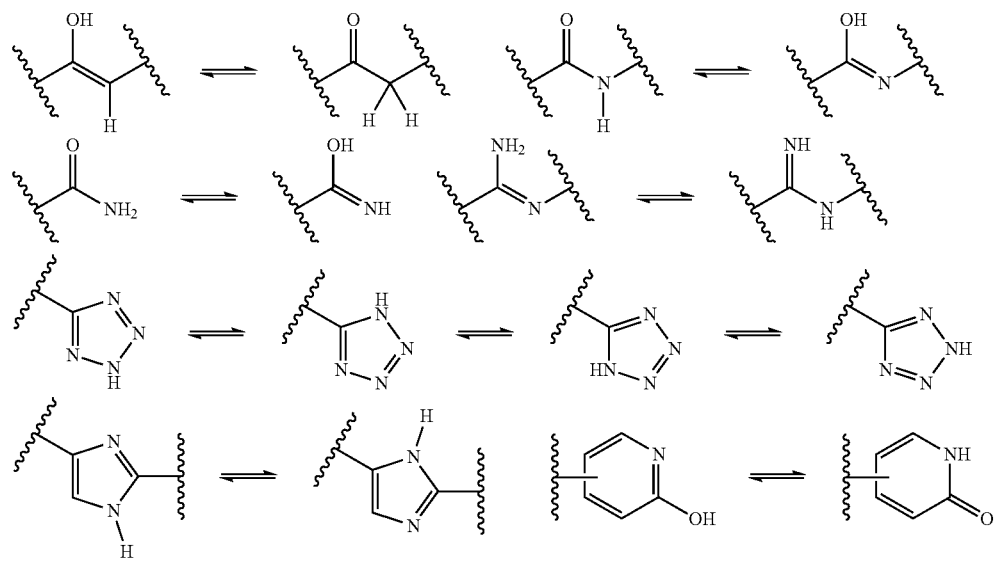

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Exemplary pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedi aniline, N-methylglucamine, glucosamine, methylglucamine, theobromine, purines, piperazine, piperidine, N-ethylpiperidine, polyamine resins and the like. See Berge et al., supra.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}$H), tritium ($^{3}$H), iodine-125 ($^{125}$I) or carbon-14 ($^{14}$C). Isotopic substitution with $^{2}$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^{1}$H atoms replaced with $^{2}$H atoms. The methods of synthesis for deuterium-containing substituted heterocyclic derivative compounds are known in the art and include, by way of non-limiting example only, the following synthetic methods.

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts, "Greene's Protective Groups in Organic Synthesis," 5th Ed., Wiley (2014), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups. Representative amine protecting groups include, but are not limited to, formyl, acetyl (Ac), trifluoroacetyl, benzyl (Bn), benzoyl (Bz), carbamate, benzyloxycarbonyl ("CBZ"), p-methoxybenzyl carbonyl (Moz or MeOZ), tertbutoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC"), p-methoxybenzyl (PMB), tosyl (Ts) and the like.

"Solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

"Salt" can include, but are not limited to, salts that retain one or more of the activities and properties of the free acids and bases and that are not undesirable. Illustrative examples of salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

"Solvent" can include, but is not limited to, non-polar, polar aprotic, and polar protic solvents. Illustrative examples of non-polar solvents include, but are not limited to, pentane, cyclopentane, hexane, cyclohexane, benzene, toluene, 1,4-dioxane, chloroform, diethyl ether, and dichloromethane (DCM). Illustrative examples of polar aprotic solvents include, but are not limited to, tetrahydrofuran (THF), ethyl acetate, acetone, dimethylformamide (DMF), acetonitrile (MeCN), dimethyl sulfoxide (DMSO), nitromethane, and propylene carbonate. Illustrative examples of polar protic solvents include, but are not limited to, formic acid, n-butanol, isopropanol (IPA), n-propanol, ethanol, methanol, acetic acid, and water.

"Acid" refers to molecules or ions capable of donating a hydron (proton or hydrogen ion H+), or, alternatively, capable of forming a covalent bond with an electron pair (e.g., a Lewis acid). Acids can include, but is not limited to, mineral acids, sulfonic acids, carboxylic acids, halogenated carboxylic acids, vinylogous carboxylic acids, and nucleic acids. Illustrative examples of mineral acids include, but are not limited to, hydrogen halides and their solutions: hydrofluoric acid (HF), hydrochloric acid (HCl), hydrobromic acid (HBr), hydroiodic acid (HI); halogen oxoacids: hypochlorous acid (HClO), chlorous acid (HClO$_2$), chloric acid (HClO$_3$), perchloric acid (HClO$_4$), and corresponding analogs for bromine and iodine, and hypofluorous acid (HFO); sulfuric acid (H$_2$SO$_4$); fluorosulfuric acid (HSO$_3$F); nitric acid (HNO$_3$); phosphoric acid (H$_3$PO$_4$); fluoroantimonic acid (HSbF$_6$); fluoroboric acid (HBF$_4$); hexafluorophosphoric acid (HPF$_6$); chromic acid (H$_2$CrO$_4$); and boric acid (H$_3$BO$_3$). Illustrative examples of sulfonic acids include, but are not limited to, methanesulfonic acid (or mesylic acid, CH$_3$SO$_3$H), ethanesulfonic acid (or esylic acid, CH$_3$CH$_2$SO$_3$H), benzenesulfonic acid (or besylic acid, C$_6$H$_5$SO$_3$H), p-toluenesulfonic acid (or tosylic acid, CH$_3$C$_6$H$_4$SO$_3$H), trifluoromethanesulfonic acid (or triflic acid, CF$_3$SO$_3$H), and polystyrene sulfonic acid (sulfonated polystyrene, [CH$_2$CH(C$_6$H$_4$)SO$_3$H]$_n$). Illustrative examples of carboxylic acids include, but are not limited to, acetic acid (CH$_3$COOH), citric acid (C$_6$H$_8$O$_7$), formic acid (HCOOH), gluconic acid (HOCH$_2$—(CHOH)$_4$—COOH), lactic acid (CH$_3$—CHOH—COOH), oxalic acid (HOOC—COOH), and tartaric acid (HOOC—CHOH—CHOH—COOH). Illustrative examples of halogenated carboxylic acids include, but are not limited to, fluoroacetic acid, trifluoroacetic acid, chloroacetic acid, dichloroacetic acid, and trichloroacetic acid. Illustrative examples of vinylogous carboxylic acids include, but are not limited to, ascorbic acid. Illustrative examples of nucleic acids include, but are not limited to, deoxyribonucleic acid (DNA) and ribonucleic acid (RNA).

"Base" refers to molecules or ions capable of accepting protons from a proton donor and/or produce hydroxide ions (OH$^-$). Illustrative examples of bases include, but are not limited to, aluminum hydroxide (Al(OH)$_3$), ammonium hydroxide (NH$_4$OH), arsenic hydroxide (As(OH)$_3$), barium hydroxide (Ba(OH)$_2$), beryllium hydroxide (Be(OH)$_2$), bismuth(III) hydroxide (Bi(OH)$_3$), boron hydroxide (B(OH)$_3$), cadmium hydroxide (Cd(OH)$_2$), calcium hydroxide (Ca(OH)$_2$), cerium(III) hydroxide (Ce(OH)$_3$), cesium hydroxide (CsOH), chromium(II) hydroxide (Cr(OH)$_2$), chromium(III) hydroxide (Cr(OH)$_3$), chromium(V) hydroxide (Cr(OH)$_5$), chromium(VI) hydroxide (Cr(OH)$_6$), cobalt(II) hydroxide (Co(OH)$_2$), cobalt(III) hydroxide (CO(OH)$_3$), copper(I) hydroxide (CuOH), copper(II) hydroxide (Cu(OH)$_2$), gallium(II) hydroxide (Ga(OH)$_2$), gallium(III) hydroxide (Ga(OH)$_3$), gold(I) hydroxide (AuOH), gold(III) hydroxide (Au(OH)$_3$), indium(I) hydroxide (MOH), indium(II) hydroxide (In(OH)$_2$), indium(III) hydroxide (In(OH)$_3$), iridium(III) hydroxide (Ir(OH)$_3$), iron(II) hydroxide (Fe(OH)$_2$), iron(III) hydroxide (Fe(OH)$_3$), lanthanum hydroxide (La(OH), lead(II) hydroxide (Pb(OH)$_2$), lead(IV) hydroxide (Pb(OH)$_4$), lithium hydroxide (LiOH), magnesium hydroxide (Mg(OH)$_2$), manganese(II) hydroxide (Mn(OH)$_2$), manganese(III) hydroxide (Mn(OH)$_3$), manganese(IV) hydroxide (Mn(OH)$_4$), manganese(VII) hydroxide (Mn(OH)$_7$), mercury(I) hydroxide (Hg$_2$(OH)$_2$), mercury(II) hydroxide (Hg(OH)$_2$), molybdenum hydroxide (Mo(OH)$_3$), neodymium hydroxide (Nd(OH)$_3$), nickel oxo-hydroxide (NiOOH), nickel(II) hydroxide (Ni(OH)$_2$), nickel(III) hydroxide (Ni(OH)$_3$), niobium hydroxide (Nb(OH)$_3$), osmium(IV) hydroxide (Os(OH)$_4$), palladium(II) hydroxide (Pd(OH)$_2$), palladium(IV) hydroxide (Pd(OH)$_4$), platinum(II) hydroxide (Pt(OH)$_2$), platinum(IV) hydroxide (Pt(OH)$_4$), plutonium(IV) hydroxide (Pu(OH)$_4$), potassium hydroxide (KOH), radium hydroxide (R$^a$(OH)$_2$), rubidium hydroxide (RbOH), ruthenium(III) hydroxide (Ru(OH)$_3$), scandium hydroxide (Sc(OH)$_3$), silicon hydroxide (Si(OH)$_4$), silver hydroxide (AgOH), sodium hydroxide (NaOH), strontium hydroxide (Sr(OH)$_2$), tantalum(V) hydroxide (Ta(OH)$_5$), technetium(II) hydroxide (Tc(OH)$_2$), tetramethylammonium hydroxide (C$_4$H$_{12}$NOH), thallium(I) hydroxide (TlOH), thallium(III) hydroxide (Tl(OH)$_3$), thorium hydroxide (Th(OH)$_4$), tin(II) hydroxide (Sn(OH)$_2$), tin(IV) hydroxide (Sn(OH)$_4$), titanium(II) hydroxide (Ti(OH)$_2$), titanium(III) hydroxide (Ti(OH)$_3$), titanium(IV) hydroxide (Ti(OH)$_4$), tungsten(II) hydroxide (W(OH)$_2$), uranyl hydroxide ((UO$_2$)$_2$(OH)$_4$), vanadium(II) hydroxide (V(OH)$_2$), vanadium(III) hydroxide (V(OH)$_3$), vanadium(V) hydroxide (V(OH)$_5$), ytterbium hydroxide (Yb(OH)$_3$), yttrium hydroxide (Y(OH)$_3$), zinc hydroxide (Zn(OH)$_2$), and zirconium hydroxide (Zr(OH)$_4$).

In certain embodiments, the processes disclosed herein can take place concurrently, in a sequential order as described herein, or in any possible order thereof.

In one aspect, disclosed herein is a process for preparing a compound of Formula (8),

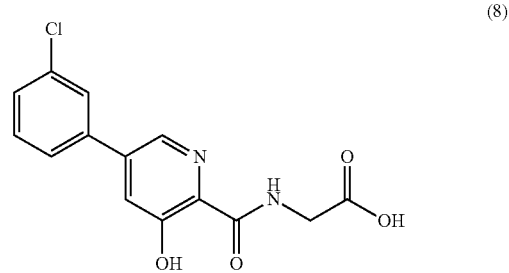 [SMILES: O=C(O)CNC(=O)c1ncc(-c2cccc(Cl)c2)cc1O]

(8)

or a salt thereof, comprising: contacting a compound of Formula (I) or a salt thereof,

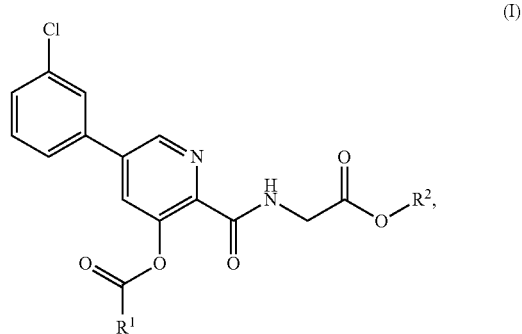

(I)

wherein R$^1$ is C$_{1-4}$ alkyl, CH$_2$Cl, phenyl, or benzyl, in which each of phenyl and benzyl may be independently substituted with one, two or three substituents selected from methyl, methoxy, nitro and halogen; and R$^2$ is C$_{1-4}$ alkyl, with a hydrolyzing agent.

In some embodiments, R$^1$ is C$_{1-4}$ alkyl, CH$_2$Cl, phenyl, or benzyl, in which each of phenyl and benzyl may be independently substituted with one or two substituents selected from methyl, methoxy, nitro and halogen. In some embodiments, R$^1$ is C$_{1-4}$ alkyl, CH$_2$Cl, phenyl, or benzyl, in which each of phenyl and benzyl may be independently substituted with one or two substituents selected from methyl, methoxy, and halogen. In some embodiments, R$^1$ is C$_{1-4}$ alkyl, CH, Cl, phenyl, or benzyl, in which each of phenyl and benzyl may be independently substituted with one or two substituents selected from methoxy and halogen. In some embodiments, $R^1$ is $C_{1-4}$ alkyl, $CH_2Cl$, phenyl, or benzyl, in which each of phenyl and benzyl may be independently substituted with one or two methoxy substituents. In some embodiments, $R^1$ is $C_{1-4}$ alkyl, $CH_2Cl$, phenyl, or benzyl. In some embodiments, $R^1$ is $C_{1-4}$ alkyl, or $CH_2Cl$. In some embodiments, $R^1$ is $C_{1-4}$ alkyl. In some embodiments, $R^1$ is t-butyl.

In some embodiments, $R^2$ is a protecting group, methyl, ethyl, propyl, isopropyl, butyl, sec-butyl, isobutyl, or tert-butyl. In some embodiments, $R^2$ is methyl, ethyl, or tert-butyl. In some embodiments, $R^2$ is methyl or tert-butyl. In some embodiments, $R^2$ is tert-butyl. In some embodiments, $R^2$ is methyl.

In some embodiments, $R^1$ is $C_{1-4}$ alkyl, $CH_2Cl$, phenyl, or benzyl, and $R^2$ is methyl, ethyl, propyl, isopropyl, butyl, sec-butyl, isobutyl, or tert-butyl. In some embodiments, $R^1$ is $C_{1-4}$ alkyl, or benzyl, and $R^2$ is methyl, ethyl, or tert-butyl. In some embodiments, $R^1$ is $C_{1-4}$, alkyl, and $R^2$ is methyl or ethyl. In some embodiments, $R^1$ tert-butyl and $R^2$ is methyl.

In some embodiments, $R^1$ is a protecting group, methylbenzene, 1,2-dimethylbenzene, 1,3-dimethylbenzene, 1,4-dimethylbenzene, 1,2,3-trimethylbenzene, 1,2,4-trimethylbenzene, 1,3,5-trimethylbenzene, methoxybenzene, 1,2-dimethoxylbenzene, 1,3-dimethoxybenzene, 1,4-dimethoxybenzene, 1,2,3-trimethoxybenzene, 1,2,4-methoxylbenzene, 1,3,5-trimethoxybenzene, nitrobenzene, 1,2-dinitrobenzene, 1,3-dinitrobenzene, 1,4-dinitrobenzene, 1,2,3-trinitrobenzene, 1,2,4-nitrolbenzene, 1,3,5-trinitrobenzene, fluorobenzene, 1,2-difluorobenzene, 1,3-difluorobenzene, 1,4-difluorobenzene, 1,2,3-trifluorobenzene, 1,2,4-fluorobenzene, 1,3,5-trifluoroberizene, chlorobenzene, 1,2-dichlorobenzene, 1,3-dichlorobenzene, 1,4-dichlorobenzene, 1,2,3-trichlorobenzene, 1,2,4-trichlorobenzene, 1,3,5-trichlorobenzene, bromobenzene, 1,2-dibromobenzene, 1,3-dibromobenzene, 1,4-dibromobenzene, 1,2,3-tribromobenzene, 1,2,4-tribromobenzene, 1,3,5-tribromobenzene, iodobenzene, 1,2-diiodobenzene, 1,3-diiodobenzene, 1,4-diiodobenzene, 1,2,3-triiodobenzene, 1,2,4-triiodobenzene, 1,3,5-triiodobenzene, 2-methylbenzyl, 3-methylbenzyl, 4-methylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 2,3-dimethoxybenzyl, 2,4-dimethoxybenzyl, 2,5-dimethoxybenzyl, 2,6-dimethoxybenzyl, 3,4-dimethoxybenzyl, 3,5-dimethoxybenzyl, 2,3-dinitrobenzyl, 2,4-dinitrobenzyl, 2,5-dinitrobenzyl, 2,6-dinitrobenzyl, 3,4-dinitrobenzyl, 3,5-dinitrobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2,3-dichlorobenzyl, 2,4-dichlorobenzyl, 2,5-dichlorobenzyl, 2,6-dichlorobenzyl, 3,4-dichlorobenzyl, 3,5-dichlorobenzyl, 2,3-dibromobenzyl, 2,4-dibromobenzyl, 2,5-dibromobenzyl, 2,6-dibromobenzyl, 3,4-dibromobenzyl, 3,5-dibromobenzyl, 2,3-diiodobenzyl, 2,4-diiodobenzyl, 2,5-diiodobenzyl, 2,6-diiodobenzyl, 3,4-diiodobenzyl, or 3,5-diiodobenzyl.

In some embodiments, $R^2$ is $C_1$-$C_{12}$ linear, $C_3$-$C_{12}$ branched or $C_3$-$C_{12}$ cyclic alkyl; $C_2$-$C_{12}$ linear, $C_3$-$C_{12}$ branched or $C_3$-$C_{12}$ cyclic alkenyl; or $C_2$-$C_{12}$ linear, $C_3$-$C_{12}$ branched or $C_3$-$C_{12}$ cyclic alkynyl, or benzyl. In some embodiments, $R^2$ is $C_1$-$C_{12}$ linear, or $C_3$-$C_{12}$ branched alkenyl; $C_2$-$C_{12}$ linear, $C_3$-$C_{12}$ or branched alkenyl; $C_2$-$C_{12}$ linear, or $C_3$-$C_{12}$ alkynyl, or benzyl. In some embodiments, $R^2$ is $C_1$-$C_{12}$ linear alkenyl; $C_2$-$C_{12}$ linear alkenyl; or $C_2$-$C_{12}$ linear alkynyl, or benzyl. In some embodiments, $R^2$ is $C_1$-$C_{12}$ linear alkenyl; $C_2$-$C_{12}$ linear alkenyl; or benzyl. In some embodiments, $R^2$ is $C_1$-$C_{12}$ linear alkenyl or benzyl. In some embodiments, $R^2$ is $C_1$-$C_{12}$ linear alkenyl.

In some embodiments, the hydrolyzing agent comprises an acid. In some embodiments, the acid is formic acid, acetic acid, propionic acid, butyric acid, valeric acid, caproic acid, oxalic acid, lactic acid, malic acid, citric acid, benzoic acid, carbonic acid, uric acid, taurine, p-toluenesulfonic acid, trifluoromethanesulfonic acid, aminomethylphosphonic acid, trifluoroacetic acid (TFA), phosphonic acid, sulfuric acid, nitric acid, phosphoric acid, hydrochloric acid, ethane sulfonic acid (ESA), or any combination thereof. In some embodiments, the acid is acetic acid, p-toluenesulfonic acid, trifluoromethanesulfonic acid, trifluoroacetic acid (TFA), sulfuric acid, or hydrochloric acid. In some embodiments, the acid is trifluoroacetic acid (TFA) or hydrochloric acid. In some embodiments, the acid is hydrochloric acid.

In some embodiments, the hydrolyzing agent comprises a base. In some embodiments, the base is an alkali metal hydroxide, alkali metal carbonate, Polymer-SK (see, e.g., MacCoss et al., Synlett, 675, 2004), or tetrabutylammonium fluoride (TBAF) (see, e.g., Ren et al., J. Am. Chem. Soc., 129, 5381, 2007). In some embodiments, the base is an alkali metal hydroxide, or tetrabutylammonium fluoride (TBAF). In some embodiments, the base is an alkali metal hydroxide. In some embodiments, the base is lithium hydroxide (LiOH), sodium hydroxide (NaOH), potassium hydroxide (KOH), or cesium hydroxide (CsOH), and any combination thereof. In some embodiments, the base is sodium hydroxide (NaOH) or potassium hydroxide (KOH). In some embodiments, the base is potassium hydroxide (KOH). In some embodiments, the base is an alkali metal carbonate. In some embodiments, the base is lithium carbonate ($Li_2CO_3$), sodium carbonate ($Na_2CO_3$), potassium carbonate ($K_2CO_3$), cesium carbonate ($Cs_2CO_3$), and any combination thereof. In some embodiments, the base is potassium carbonate ($K_2CO_3$) or cesium carbonate ($Cs_2CO_3$). In some embodiments, the base is cesium carbonate ($Cs_2CO_3$).

In some embodiments, the contacting occurs in presence of a solvent. In some embodiments, the solvent comprises N,N-dimethylformide (DMF), t-butanol, dimethoxyethane (DME), acetonitrile, dichloromethane (DCM), tetrahydrofuran (THF), 2-methyltetrahydrofuran (ME-THF), isopropyl alcohol, methanol, ethanol, or any combination thereof. In some embodiments, the solvent comprises THF. In some embodiments, the solvent comprises N,N-dimethylformide (DMF), dimethoxyethane (DME), tetrahydrofuran (THF), or 2-methyltetrahydrofuran (ME-THF). In some embodiments, the solvent comprises 2-methyltetrahydrofuran (ME-THF).

In some embodiments, the purity of the compound of Formula (8) is at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (8) is at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (8) is at least 99%, at least 99.1%, at least 99.2%, at least 99.3%, at least 99.4%, at least 99.5%, at least 99.6%, at least 99.7%, at least 99.8%, at least 99.9%. In some embodiments, the purity of the compound of Formula (8) is at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (8) is at least 99%.

In some embodiments, disclosed herein is a process for preparing a compound of Formula (I),

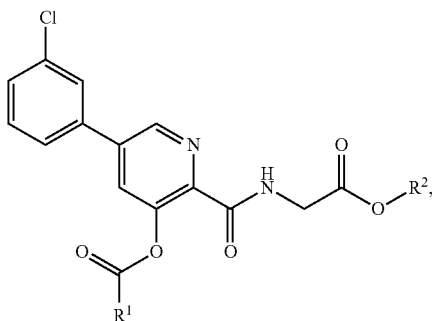

comprising:

a) contacting the compound of Formula (5) or a salt thereof,

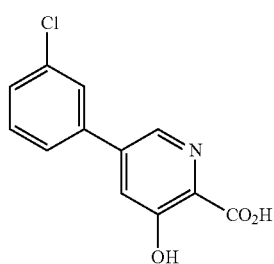

with a compound of Formula (II) or a salt thereof in the presence of a base,

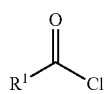

wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen;

b) contacting a product formed in step a) with a compound of Formula (III) or a salt thereof in the presence of a base,

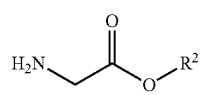

wherein $R^2$ is $C_{1-4}$ alkyl;

to provide the compound of Formula (I) or a salt thereof,

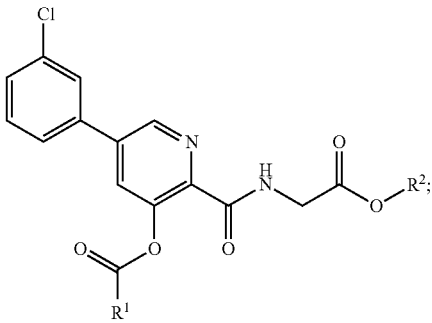

and c) optionally washing a product formed in step b) with a solvent comprising water and base.

In some embodiments, a small amount of a compound of Formula (IV) may be formed after step b) or step c). The compound of Formula (I) along with the compound of Formula (IV) can be converted directly to the compound of Formula (8) via hydrolysis as described herein.

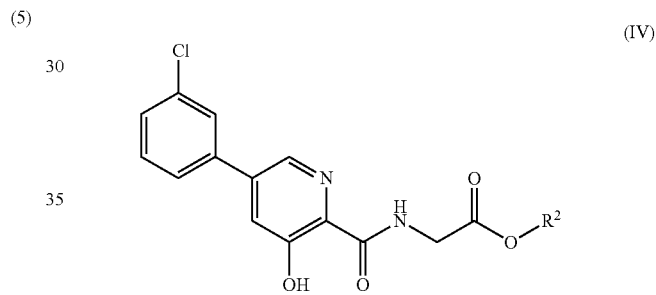

In some embodiments, $R^1$ is $C_{1-4}$ alkyl, $CH_2Cl$, phenyl, or benzyl, in which each of phenyl and benzyl may be independently substituted with one or two substituents selected from methyl, methoxy, nitro and halogen. In some embodiments, $R^1$ is $C_{1-4}$ alkyl, $CH_2Cl$, phenyl, or benzyl, in which each of phenyl and benzyl may be independently substituted with one or two substituents selected from methyl, methoxy, and halogen. In some embodiments, $R^1$ is $C_{1-4}$ alkyl, $CH_2Cl$, phenyl, or benzyl, in which each of phenyl and benzyl may be independently substituted with one or two substituents selected from methoxy and halogen. In some embodiments, $R^1$ is $C_{1-4}$ alkyl, $CH_2Cl$, phenyl, or benzyl, in which each of phenyl and benzyl may be independently substituted with one or two methoxy substituents. In some embodiments, $R^1$ is $C_{1-4}$ alkyl, $CH_2Cl$, phenyl, or benzyl. In some embodiments, $R^1$ is $C_{1-4}$ alkyl, or $CH_2Cl$. In some embodiments, $R^1$ is $C_{1-4}$ alkyl. In some embodiments, $R^1$ is t-butyl.

In some embodiments, $R^2$ is a protecting group, methyl, ethyl, propyl, isopropyl, butyl, sec-butyl, isobutyl, or tert-butyl. In some embodiments, $R^2$ is methyl, ethyl, or tert-butyl. In some embodiments, $R^2$ is methyl or tert-butyl. In some embodiments, $R^2$ is methyl. In some embodiments, $R^1$ is t-butyl, and $R^2$ is methyl.

In some embodiments, the contacting occurs in presence of a base. In some embodiments, the base is independently an organic base. In some embodiments, the organic base is triethylamine (TEA), triisopropylamine, diisopropylamine (DIPEA), pyridine, 2,6-Di-tert-butylpyridine, 1,8-Diazabicycloundec-7-ene (DBU), 1,5-Diazabicyclo(4.3.0)non-5- ene (DBN), or any combination thereof. In some embodiments, the organic base is triethylamine (TEA), diisopropylamine (DIPEA), pyridine, or 1,8-Diazabicycloundec-7-ene (DBU). In some embodiments, the organic base is triethylamine (TEA) or diisopropylamine (DIPEA). In some embodiments, the organic base is diisopropylamine (DIPEA).

In some embodiments, the contacting occurs in presence of a solvent. In some embodiments, the solvent comprises ethanol, N,N-dimethylformide (DMF), diethylformamide (DEF), dimethylacetamide (DMA), diethylacetamide (DEA), dimethyl sulfoxide(DMSO), dioxane, dimethoxyethane (DME), acetonitrile, dichloromethane (DCM), tetrahydrofuran (THF), 2-methyltetrahydrofuran (ME-THF), or any combination thereof. In some embodiments, the solvent comprises ethanol, N,N-dimethylformide (DMF), dimethylacetamide (DMA), dimethyl sulfoxide(DMSO), dichloromethane (DCM), tetrahydrofuran (THF), or 2-methyltetrahydrofuran (ME-THF). In some embodiments, the solvent comprises N,N-dimethylformide (DMF), tetrahydrofuran (THF), or 2-methyltetrahydrofuran (ME-THF). In some embodiments, the solvent comprises N,N-dimethylformide (DMF) or tetrahydrofuran (THF). In some embodiments, the solvent comprises tetrahydrofuran (THF).

In some embodiments, step c) is required. In some embodiments, the product formed in step c) comprises less than about 0.5% of the compound of Formula (5). In some embodiments, the product formed in step c) comprises less than about 0.4% of the compound of Formula (5). In some embodiments, the product formed in step c) comprises less than about 0.3% of the compound of Formula (5). In some embodiments, the product formed in step c) comprises less than about 0.2% of the compound of Formula (5). In some embodiments, the product formed in step c) comprises less than about 0.1% of the compound of Formula (5). In some embodiments, the product formed in step c) comprises less than about 0.09% of the compound of Formula (5). In some embodiments, the product formed in step c) comprises less than about 0.08% of the compound of Formula (5). In some embodiments, the product formed in step c) comprises less than about 0.07% of the compound of Formula (5). In some embodiments, the product formed in step c) comprises less than about 0.06% of the compound of Formula (5). In some embodiments, the product formed in step c) comprises less than about 0.05% of the compound of Formula (5). In some embodiments, the product formed in step c) comprises less than about 0.04% of the compound of Formula (5). In some embodiments, the product formed in step c) comprises less than about 0.03% of the compound of Formula (5). In some embodiments, the product formed in step c) comprises less than about 0.02% of the compound of Formula (5). In some embodiments, the product formed in step c) comprises less than about 0.01% of the compound of Formula (5).

In some embodiments, the solvent used in step c) comprises water and a base. In some embodiments, the water to base ratio (v/v) is about 0.1%-1%, about 0.1%-5%, about 0.1-10%, about 0.1%-20%, about 0.5%-1%, about 0.5%-5%, about 0.5%40%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, or about 95%-99%. In some embodiments, the base is an organic base. In some embodiments, the organic base is triethylamine (TEA), triisopropylamine, di isopropylamine (DIPEA), pyridine, 2,6-Di-tert-butylpyridine, 1,8-Diazabicycloundec-7-ene (DBU), 1,5-Diazabicyclo(4.3.0)non-5-ene (DBN), or any combination thereof. In some embodiments, the organic base is triethylamine (TEA), diisopropylamine (DIPEA), pyridine, or 1,8-Diazabicycloundec-7-ene (DBU). In some embodiments, the organic base is triethylamine (TEA) or diisopropylamine (DIPEA). In some embodiments, the organic base is diisopropylamine (DIPEA).

In another aspect, disclosed herein is a compound of Formula (I):

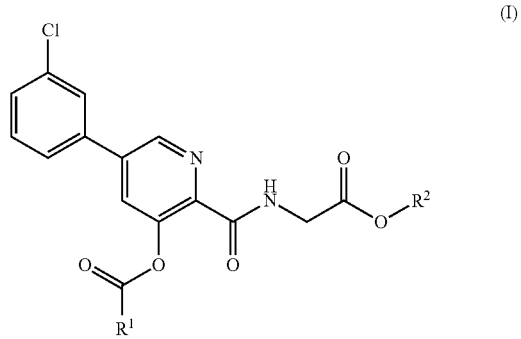

(I)

or a salt thereof, wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl.

In some embodiments, the purity of the compound of Formula (I) is at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of compound of Formula (I) is at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (I) is at least at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (I) is at least 99%, at least 99.1%, at least 99.2%, at least 99.3%, at least 99.4%, at least 99.5%, at least 99.6%, at least 99.7%, at least 99.8%, or at least 99.9%. In some embodiments, the purity of the compound of Formula (I) is at least 99%.

In some embodiments, the compound of Formula (I) comprises less than about 0.5% of the compound of Formula (5), i.e., the compound of Formula (I) contains less than about 0.5% of an impurity that is the compound of Formula (5). Throughout the claims and specification, the sentence of "the compound of Formula (I) comprises less than about X % of the compound of Formula (5)" means that the compound of Formula (I) contains less than about X % of an impurity that is the compound of Formula (5). In some embodiments, the compound of Formula (I) comprises less than about 0.4% of the compound of Formula (5). In some embodiments, the compound of Formula (I) comprises less than about 0.3% of the compound of Formula (5). In some embodiments, the compound of Formula (I) comprises less than about 0.2% of the compound of Formula (5). In some embodiments, the compound of Formula (I) comprises less than about 0.1% of the compound of Formula (5). In some embodiments, the compound of Formula (I) comprises less than about 0.09% of the compound of Formula (5). In some embodiments, the compound of Formula (I) comprises less than about 0.08% of the compound of Formula (5). In some embodiments, the compound of Formula (I) comprises less than about 0.07% of the compound of Formula (5). In some embodiments, the compound of Formula (I) comprises less than about 0.06% of the compound of Formula (5). In some embodiments, the compound of Formula (I) comprises less than about 0.05% of the compound of Formula (5). In some embodiments, the compound of Formula (I) comprises less than about 0.04% of the compound of Formula (5). In some embodiments, the compound of Formula (I) comprises less than about 0.03% of the compound of Formula (5). In some embodiments, the compound of Formula (I) comprises less than about 0.02% of the compound of Formula (5). In some embodiments, the compound of Formula (I) comprises less than about 0.01% of the compound of Formula (5).

In another aspect, disclosed herein is a composition comprising:
a) 80% or more of a compound of Formula (I) or a salt thereof,

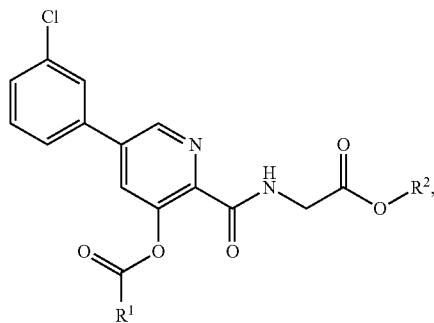
(I)

wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and $R^2$ is $C_{1-4}$ alkyl;
b) 20% or less of a compound of Formula (IV) or a salt thereof,

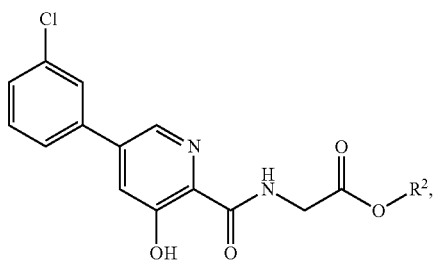
(IV)

wherein $R^1$ is $C_{1-4}$ alkyl, and wherein the combined amount of the compound of Formula (I) or a salt thereof and the compound of Formula (IV) or a salt thereof is between about 99% and about 100%, for example, at about 99.1%, about 99.2%, about 99.3%, about 99.4%, about 99.5%, about 99.6%, about 99.7%, about 99.8%, or about 99.9%.

In some embodiments, $R^2$ is a protecting group, methyl, ethyl, propyl, isopropyl, butyl, sec-butyl, isobutyl, or tert-butyl. In some embodiments, $R^2$ is methyl, ethyl, or tert-butyl. In some embodiments, $R^2$ is methyl or tert-butyl. In some embodiments, $R^2$ is methyl.

In some embodiments, the composition comprises about 85% or more of a compound of Formula (I) or a salt thereof and about 15% or less of the compound of Formula (IV) or a salt thereof. In some embodiments, the composition comprises about 90% or more of a compound of Formula (I) or a salt thereof and about 10% or less of the compound of Formula (IV) or a salt thereof. In some embodiments, the composition comprises about 95% or more of a compound of Formula (I) or a salt thereof and about 5% or less of the compound of Formula (IV) or a salt thereof. In some embodiments, the composition comprises 99% or more of a compound of Formula (I) or a salt thereof and about 1% or less of the compound of Formula (IV) or a salt thereof.

In some embodiments, the composition comprises less than about 0.5% of the compound of Formula (5). In some embodiments, the composition comprises less than about 0.4% of the compound of Formula (5). In some embodiments, the composition comprises less than about 0.3% of the compound of Formula (5). In some embodiments, the composition comprises less than about 0.2% of the compound of Formula (5). In some embodiments, the composition comprises less than about 0.1% of the compound of Formula (5). In some embodiments, the composition comprises less than about 0.05% of the compound of Formula (5). In some embodiments, the composition comprises less than about 0.01% of the compound of Formula (5).

In another aspect, disclosed herein is a composition comprising a compound of Formula (I) or a salt thereof,

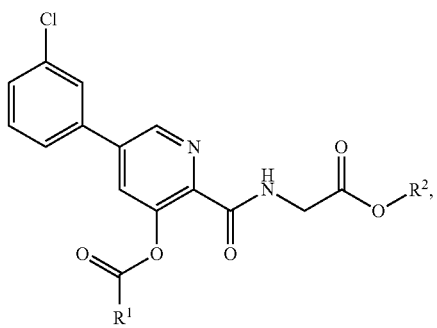
(I)

wherein $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; $R^2$ is $C_{1-4}$ alkyl; and comprising less than about 0.5% of the compound of Formula (5):

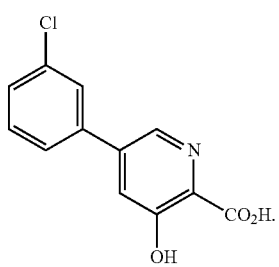

In some embodiments, the composition comprises less than about 0.4% of the compound of Formula (5). In some embodiments, the composition comprises less than about 0.3% of the compound of Formula (5). In some embodiments, the composition comprises less than about 0.2% of the compound of Formula (5). In some embodiments, the composition comprises less than about 0.1% of the compound of Formula (5). In some embodiments, the composition comprises less than 0.05% of the compound of Formula (5). In some embodiments, the composition comprises less than about 0.01% of the compound of Formula (5).

Throughout the claims and specification, unless otherwise noted, a numeric percentage point (%) of a compound refers to the purity or impurity of that compound as measured by HPLC.

Methods of Preparation

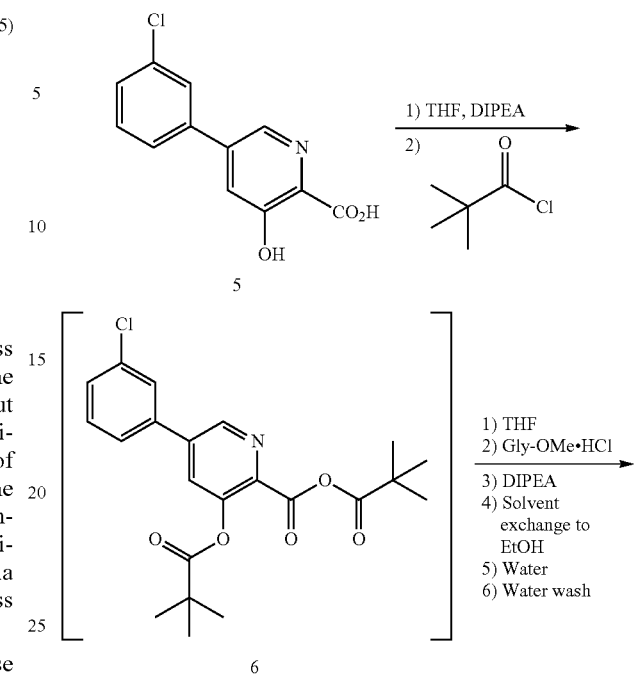

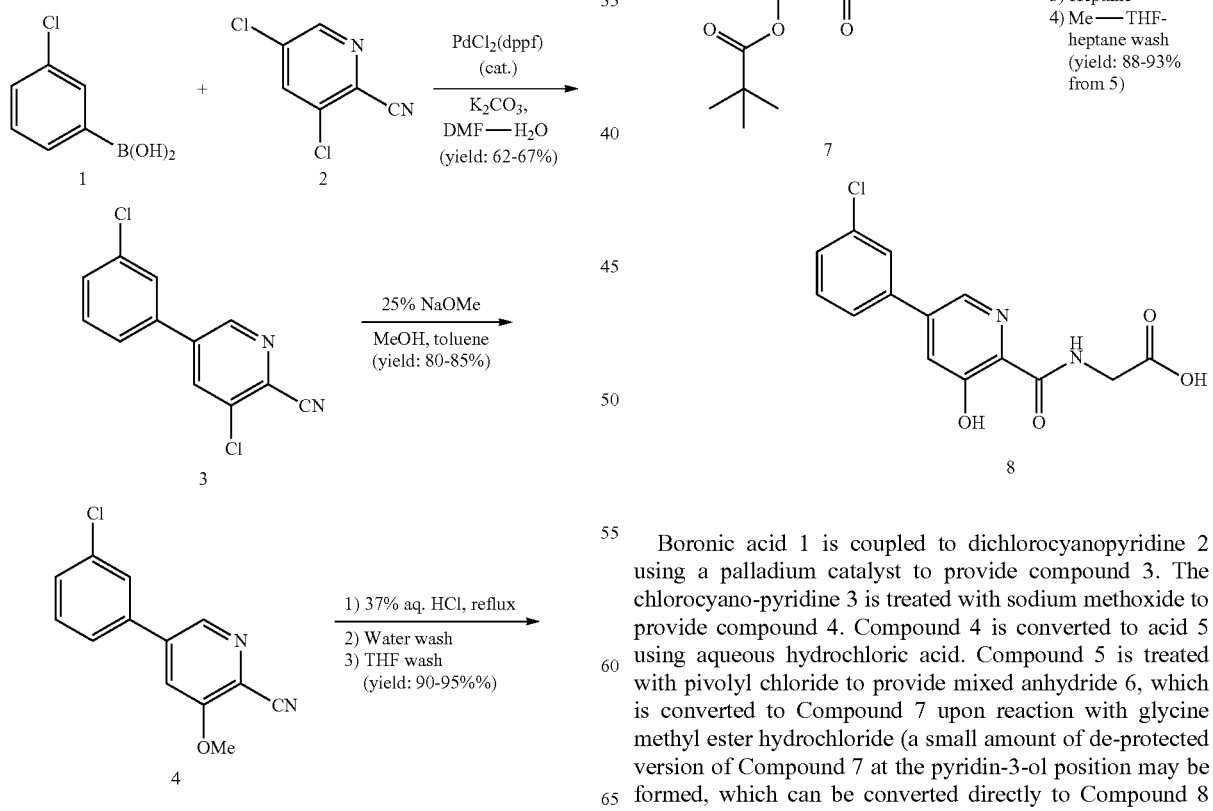

Boronic acid 1 is coupled to dichlorocyanopyridine 2 using a palladium catalyst to provide compound 3. The chlorocyano-pyridine 3 is treated with sodium methoxide to provide compound 4. Compound 4 is converted to acid 5 using aqueous hydrochloric acid. Compound 5 is treated with pivolyl chloride to provide mixed anhydride 6, which is converted to Compound 7 upon reaction with glycine methyl ester hydrochloride (a small amount of de-protected version of Compound 7 at the pyridin-3-ol position may be formed, which can be converted directly to Compound 8 without further purification). Compound 7 is converted to compound 8 using potassium hydroxide.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed with invention as defined in the claims which follow. The invention disclosed herein is further illustrated by the following examples which in no way should be construed as being limiting.

Example 1: Preparation of 5-(3-chlorophenyl)-3-chloro-2-cyanopyridine (Compound 3)

A 20 L reactor equipped with a mechanical stirrer, dip tube, thermometer and nitrogen inlet was charged with (3-chlorophenyl)boronic acid (550 g, 3.52 mol), 3,5-dichloro-2-cyanopyridine (639 g, 3.69 mol), $K_2CO_3$ (5.5 g, 40 mmol), [1,1'-bis(diphenyphosphino)ferrocene]dichloro-palladium(II) [$PdCl_2$(dppf)] (11.5 g, 140 mmol), and dimethylformamide (3894 g, 4.125 L). The reaction solution was agitated and purged with nitrogen through the dip-tube for 30 minutes. Degassed water (413 g) was then charged to the reaction mixture while maintaining a temperature of less than 50° C. 25 hours. The reaction was determined to be complete due to the disappearance of 3,5-dichloro-2-cyanopyridine as measured by TLC analysis using ethyl acetate/methanol (4:1) as the mobile phase and UV 435 nm to visualize the reaction components. The reaction solution was then cooled to 5° C. and charged with heptane (940 g, 1.375 L) and agitated for 30 minutes. Water (5.5 L) was charged and the mixture was further agitated for 1 hour as the temperature was allowed to rise to 15° C. The solid product was isolated by filtration and washed with water (5.5 L) followed by heptane (18881 g, 2750 ML). The resulting cake was air dried under vacuum for 18 hours and then triturated with a mixture of 2-propanol (6908 g, 8800 mL and heptane (1 g, 2200 mL at 50° C. for 4 hours, cooled to ambient temperature and then agitated at ambient temperature for 1 hour. The product was then isolated by filtration and washed with cold 2-propanol (3450 g, 4395 mL) followed by heptane (3010 g, 4400 mL). The resulting solid was dried under high vacuum at 40° C. for 64 hours to afford 565.9 g (65% yield) of the desired product as a beige solid. Purity by HPLC was 98.3%. $^1$H NMR (DMSO-$d_6$) δ 9.12 (d, 1H), 8.70 (d, 1H), 8.03 (t, 1H) 7.88 (m, 1H), and 7.58 (m, 2H).

Example 2: Preparation of 5-(3-chlorophenyl)-3-methoxy-2-cyanopyridine (Compound 4)

A 20 L reactor equipped with a mechanical stirred, condenser, thermometer and nitrogen inlet was charged with 5-(3-chlorophenyl)-3-chloro-2-cyanopyridine, 1, (558 g, 2.24 mol) and methanol as needed, followed by sodium methoxide (25% solution in methanol, 726.0 g, 3.36 mol). With agitation, the reaction solution was heated to reflux for 24 hours, resulting in a beige-colored suspension. The reaction was determined to be complete due to the disappearance of 5-(3-chlorophenyl)-3-chloro-2-cyanopyridine as measured by TLC analysis using hexane/ethyl acetate (6:3) as the mobile phase and UV 435 nm to visualize the reaction components. The reaction mixture was cooled to 5° C. and then charged with water (5580 mL). The resulting slurry was agitated for 3 hours at 5° C. The solid product was isolated by filtration and washed with water (5580 mL) until the filtrate had a pH of 7. The filter cake was air dried under vacuum for 16 hours. The filter cake was then charged back to the reactor and triturated in MeOH (2210 g, 2794 mL) for 1 hour at ambient temperature. The solid was collected by filtration and washed with MeOH (882 g, 1116 mL, 5° C.) followed by heptane (205 mL, 300 mL), and dried under high vacuum at 45° C. for 72 hours to afford 448 g (82% yield) of the desired product as an off-white solid. Purity by HPLC was 97.9%. $^1$H NMR (DMSO-$d_6$) δ 8.68 (d, 1H), 8.05 (d, 1H), 8.01 (s, 1H) 7.86 (m, 1H), 7.59 (s, 1H), 7.57 (s, 1H) and 4.09 (s, 3H).

Example 3: Preparation of 5-(3-chlorophenyl)-3-hydroxypyridine-2-carboxylic acid (Compound 5)

A 20 L reactor equipped with a mechanical stirrer, condenser, thermometer, nitrogen inlet and 25% aqueous NaOH trap was charged 5-(3-chlorophenyl)-3-methoxy-2-cyanopyridine, 2, (440.6 g, 1.8 mol) and 37% aqueous solution of HCl (5302 g). While being agitated, the reaction solution was heated to 102° C. for 24 hours. Additional 37% aqueous HCl (2653 g) was added followed by agitation for 18 hours at 104° C. The reaction contents was then cooled to 5° C., charged with water (4410 g) and then agitated at 0° C. for 16 hours. The resulting precipitated product was isolated by filtration and washed with water until the filtrate had a pH of 6 (about 8,000 L of water). The filter cake was pulled dry under reduced pressure for 2 hours. The cake was then transferred back into the reactor and triturated in THF (1958 g, 2201 mL) at ambient temperature for 2 hours. The solid product was then isolated by filtration and washed with THF (778 g, 875 mL) and dried under reduced pressure at 5° C. for 48 hours to afford 385 g (89% yield) of the desired product as an off-white solid. HPLC purity was 96.2%. $^1$H NMR (DMSO-$d_6$) δ 8.52 (d, 1H), 7.99 (d, 1H), 7.95 (s, 1H) 7.81 (t, 1H), 7.57 (s, 1H), and 7.55 (s, 1H).

Example 4a: Preparation of 5-(3-chlorophenyl)-2-(N-glycine methylester carboxylic amide)-3-(2,2-dimethyl-1-oxopropoxy) pyridine (Compound 7)

3-Hydroxy 5-(3-chlorophenyl)-2-carboxy-pyridine (1.00 wt) and tetrahydrofuran (4.48 wt/wt) was charged to a reactor, followed by N,N-diisopropyethylamine (1.21 wt/wt). Pivaloyl chloride (1.05 wt/wt) was added at about 0° C. and the mixture was agitated until the reaction was deemed to be completed. Tetrahydrofuran (2.59 wt/wt) and glycine methyl ester hydrochloride (0.64 wt/wt) were added at about 0° C. and N,N-diisopropyethylamine (0.78 wt/wt) was added at about 0° C. The mixture was agitated at about 0° C. and at ambient temperature until the reaction was deemed completed. The reaction solvent tetrahydrofuran was exchanged for ethanol at elevated temperature under vacuum. Water (8.00 wt/wt) was added at about 40° C. The resulting suspension was agitated at ambient temperature, filtered and washed with ethanol and water. Isolated Compound 7 contained about 0.5% of Compound 5, which was difficult to remove.

Example 4b: Preparation of 5-(3-chlorophenyl)-2-(N-glycine methylester carboxylic amide)-3-(2,2-dimethyl-1-oxopropoxy) pyridine (Compound 7)

3-Hydroxy 5-(3-chlorophenyl)-2-carboxy-pyridine (1.00 wt) and tetrahydrofuran (4.48 wt/wt) was charged to a reactor, followed by N,N-diisopropyethylamine (1.21 wt/wt). Pivaloyl chloride (1.05 wt/wt) was added at about 0° C. and the mixture was agitated until the reaction was deemed to be completed. Tetrahydrofuran (2.59 wt/wt) and glycine methyl ester hydrochloride (0.64 wt/wt) were added at about 0° C. and N,N-diisopropyethylamine (0.78 wt/wt) was added at about 0° C. The mixture was agitated at about 0° C. and at ambient temperature until the reaction was deemed completed. The reaction solvent tetrahydrofuran was exchanged for ethanol at elevated temperature under vacuum. Water (8.00 wt/wt) was added at about 40° C., followed by an additional amount of N,N-diisopropyethylamine (0.077 wt/wt). The suspension was agitated at ambient temperature, filtered and washed with ethanol and water. Isolated Compound 7 contained no detectable amount of Compound 5 or lower than 0.05% of Compound 5 by HPLC. Compound 7 was used for the subsequent step without further purification. $^1$H NMR (300 MHz, DMSO-$d_6$) δ 9.064 (t, j=6.1 Hz, 1H), 8.947 (d, j=2.0 Hz, 1H), 8.161 (d, j=2.0 Hz, 1H), 7.999 (m, 1H), 7.870 (m, 1H), 7.568 (m, 2H), 4.024 (d, j=6.1 Hz, 2H), 3.656 (s, 3H), 1.332 (s, 9H). The molecular weight of Compound 7 is 404.11, which was confirmed by its mass spectrum showing a main peak with a mass of 405.1, which is the [M+1] ion of the molecule.

Example 5: Preparation of 5-(3-chlorophenyl)-2-(N-glycine carboxylic amide)-3-hydroxypyridine (Compound 8)

5-(3-chlorophenyl)-2-(N-glycine methylester carboxylic amide)-3-(2,2-dimethyl-1-oxopropoxy) pyridine, 2-methyl-tetrahydrofuran (6.92 wt/wt) and water (3.24 wt/wt) were charged into a reactor. A potassium hydroxide solution of approximately 45% (1.50 wt/wt) was added and the mixture agitated at ambient temperature until the reaction was deemed to be completed. Water ((3.73 wt/wt) was charged and the mixture was acidified with concentrated aqueous HCl (about 1.3 wt/wt) at ambient temperature. The lower aqueous phase was discharged, and water was added to the organic extract at about 45° C. The lower aqueous phase was discharged and the organic phase was polish filtered. 2-Methyl-tetrahydrofuran (8.30 wt/wt) was charged and the mixture concentrated at about 45° C. under vacuum to about 5 volumes. n-Heptane (0.99 wt/wt) was and 5-(3-chlorophenyl)-2-(N-glycine carboxylic amide)-3-hydroxypyridine seeds (0.005 wt/wt) were added at about 45° C. n-Heptane (5.62 wt/wt) was charged in about 2 h and the suspension was agitated for about 1 h at about 45° C. The suspension was concentrated to about 6.5 volumes at elevated temperature under vacuum, followed by agitation at about 75° C. The suspension was cooled to ambient temperature, agitated and filtered. The wet cake was washed with n-heptane (3.31 wt/wt) and dried at about 50° C. and vacuum to yield white to beige crystals in about 90% yield and a purity of about 100% by HPLC from the charged amount of 3-hydroxy 5-(3-chlorophenyl)-2-carboxy-pyridine (Compound 5). $^1$H NMR (DMSO-$d_6$) δ 12.84 (s, 1H), 12.39 (s, 1H), 9.39 (t, 1H), 8.56 (d, 1H), 7.94 (s, 1H), 7.81 (m, 2H), 7.55 (q, 2H), and 4.02 (d, 2H).

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I):

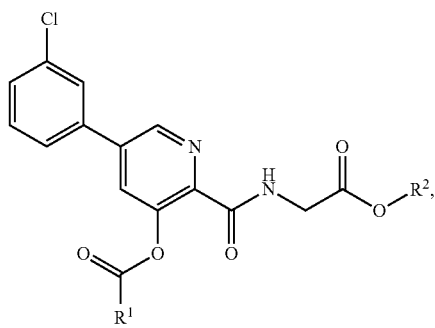

or a salt thereof, wherein:
$R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen; and
$R^2$ is $C_{1-4}$ alkyl; and
wherein the compound comprises less than about 0.5% of the compound of Formula (5):

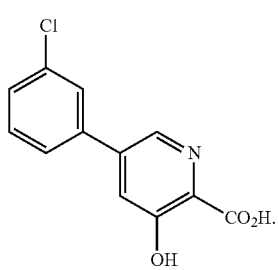

2. The compound of claim 1 or a salt thereof, wherein $R^1$ is t-butyl and/or $R^2$ is methyl.

3. The compound of claim 1 or a salt thereof, which is at least about 80% pure, about 85% pure, about 90% pure, or about 95% pure.

4. The compound of claim 1 or a salt thereof, wherein the compound comprises less than about 0.3% of the compound of Formula (5).

5. The compound of claim 1 or a salt thereof, wherein the compound comprises less than about 0.2% of the compound of Formula (5).

6. The compound of claim 1 or a salt thereof, wherein the compound comprises less than about 0.1% of the compound of Formula (5).

7. The compound of claim 1 or a salt thereof, wherein the compound comprises less than about 0.05% of the compound of Formula (5).

8. The compound of claim 1 or a salt thereof, wherein the compound of Formula (I) is isolated.

9. A composition comprising:
a) 80% or more of a compound of Formula (I) or a salt thereof,

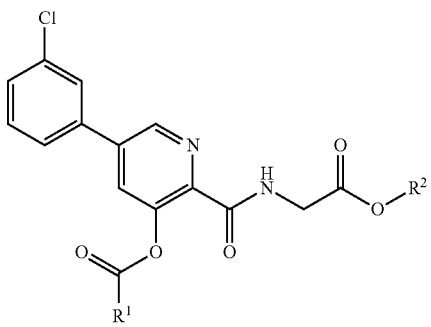

wherein:
- $R^1$ is $C_{1-4}$ alkyl, $CH_2Cl$, phenyl, or benzyl, in which each of phenyl and benzyl may be independently substituted with one, two or three substituents selected from methyl, methoxy, nitro and halogen;
- $R^2$ is $C_{1-4}$ alkyl; and b) 20% or less of a compound of Formula (IV) or a salt thereof,

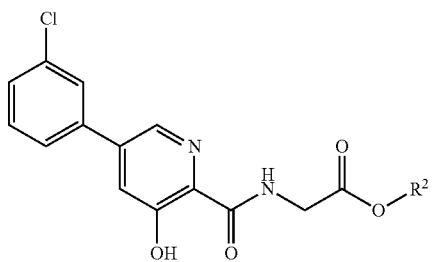

wherein $R^2$ is $C_{1-4}$ alkyl;

wherein the composition comprises less than about 0.5% of the compound of Formula (5):

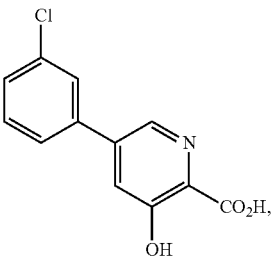

and
wherein the combined amount of the compound of Formula (I), or a salt thereof, and the compound of Formula (IV), or a salt thereof, is between about 99% and about 100% of the composition.

10. The composition of claim 9, wherein $R^1$ is t-butyl and or $R^2$ is methyl.

11. The composition of claim 9, comprising 85% or more of the compound of Formula (I), or a salt thereof, and 15% or less of the compound of Formula (IV), or a salt thereof.

12. The composition of claim 9, comprising 90% or more of the compound of Formula (I), or a salt thereof, and 10% or less of the compound of Formula (IV), or a salt thereof.

13. The composition of claim 9, comprising less than about 0.3% of the compound of Formula (5).

14. The composition of claim 9, comprising less than about 0.2% of the compound of Formula (5).

15. The composition of claim 9, comprising less than about 0.1% of the compound of Formula (5).

16. The composition of claim 9, comprising less than about 0.05% of the compound of Formula (5).

17. The compound of claim 3, wherein purity is as measured by HPLC.

* * * * *

UNITED STATES PATENT AND TRADEMARK OFFICE
CERTIFICATE OF CORRECTION

PATENT NO. : 12,269,802 B2
APPLICATION NO. : 18/334101
DATED : April 8, 2025
INVENTOR(S) : Boris I. Gorin et al.

Page 1 of 1

It is certified that error appears in the above-identified patent and that said Letters Patent is hereby corrected as shown below:

In the Claims

Claim 10, Column 26, Lines 21-22:
Delete "and or"
Replace with --and/or--

Signed and Sealed this
Seventeenth Day of June, 2025

Coke Morgan Stewart
*Acting Director of the United States Patent and Trademark Office*